United States Patent [19]

Frommer et al.

[11] 4,062,950
[45] Dec. 13, 1977

[54] AMINO SUGAR DERIVATIVES

[75] Inventors: Werner Frommer; Bodo Junge; Uwe Keup; Lutz Müller; Walter Puls; Delf Schmidt, all of Wuppertal, Germany

[73] Assignee: Bayer Aktiengesellschaft, Germany

[21] Appl. No.: 654,627

[22] Filed: Feb. 2, 1976

Related U.S. Application Data

[63] Continuation-in-part of Ser. No. 506,550, Sept. 16, 1974, abandoned.

[30] Foreign Application Priority Data

Sept. 22, 1973  Germany .............................. 2347782

[51] Int. Cl.$^2$ ...................... A61K 31/71; C07H 15/20
[52] U.S. Cl. .................................. 424/181; 195/80 R; 260/307 DB; 536/4; 536/17; 536/18
[58] Field of Search .............. 536/17, 4, 18; 424/181; 195/80 R; 260/307 DB; 421/181

[56] References Cited

U.S. PATENT DOCUMENTS

| | | | |
|---|---|---|---|
| 3,808,198 | 4/1974 | Naito et al. | 536/17 |
| 3,870,698 | 3/1975 | Munakata et al. | 536/17 |
| 3,876,766 | 4/1975 | Frommer et al. | 424/115 |

*Primary Examiner*—Johnnie R. Brown
*Attorney, Agent, or Firm*—Jacobs & Jacobs

[57] ABSTRACT

New amino sugars which are glucopyranosyl and oligoglucosidyl derivatives of 4,6-bisdesoxy-4-(4,5,6-trihydroxy-3-hydroxymethylcyclohex-2-en-1-ylamino)-α-D-glucopyranose inhibit glycoside hydrolases of the digestive tract. The compounds, of which O-{4,6-bisdesoxy-4-[1S-(1,4,6/5)-4,5,6-trihydroxy-3-hydroxymethylcyclohex-2-en-1-ylamino]-α-D-glucopyranosyl}-(1→4)-O-α-D-glucopyranosyl-(1→4)-D-glucopyranose is a representative embodiment, demonstrate both saccharase and amylase inhibiting properties.

30 Claims, No Drawings

AMINO SUGAR DERIVATIVES

CROSS-REFERENCE

This is a continuation-in-part of Ser. No. 506,550 filed Sept. 16, 1974 now abandoned.

DETAILED DESCRIPTION

The present invention relates to amino sugar derivatives, to processes for their production, to pharmaceutical compositions wherein said compounds are the active agent, and to methods of controlling carbohydrate metabolism in humans and animals by inhibiting glucoside hydrolase with such compounds, as in the treatment of diabetes, adiposity and hyperlipemia.

It is known that a number of microorganisms of the order Actinomycetes, particularly those of the family Actinoplanaceae, produce materials which inhibit glycoside hydrolases. U.S. Pat. No. 3,876,766, for example, describes methods for producing such materials from a number of such microorganisms. The materials obtained fall into two broad groups: (a) oligosaccharides or polysaccharide derivatives and (b) inhibitors of a peptide nature.

U.S. Pat. No. 3,855,066 describes an improvement in which materials having significantly higher levels of amylase activity are obtained from Actinoplanaceae CBS strain 614.71, preferably by culturing in the presence of 4 to 6% starch.

U.S. Pat. No. 3,879,546 describes a further refinement in which polysaccharidic or oligosaccharidic materials having primarily amylase inhibiting properties can be converted to materials having a higher level of saccharase inhibiting properties through hydrolytic techniques (acidic or enzymatic hydrolysis) by which mono-, di- and trisaccharide units are cleaved from the inhibitor molecules. The properties of the products in terms of saccharase/amylase inhibitory activity appear to be a function of the hydrolysis conditions (as well as the properties of the starting amylase inhibitor which, in turn, depends upon the microorganism and culture conditions).

The direct preparation of materials having predominantly saccharase inhibiting properties through the use of a starch free nutrient solution, preferably in the presence of maltose, has also been described in copending application Ser. No. 481,224, now U.S. Pat. No. 3,937,817.

These references thus teach a number of variations in the basic technique of culturing microorganisms of the order Actinomycetes which variations produce materials having significantly different inhibitory properties. While none of these prior art materials appear to represent a single, molecularly homogeneous product, it would appear that those materials having longer oligosaccharide chains are primarily amylase inhibitors and thus block the conversion of starch or glycogen to maltose by amylase whereas the materials having relatively shorter oligosaccharide chains do not have this property but act primarily on the conversion of sucrose to glucose and fructose by saccharase.

The present invention pertains to certain new amino sugars which are pure and which in their pure state, exhibit highly advantageous and unexpected properties in their patterns of enzyme inhibition.

The present invention embraces the three individual amino sugar derivatives falling within the formula:

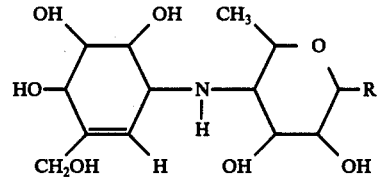

wherein R is a monosaccharide or an oligosaccharide chain of 2 or 3 monosaccharide units, in particular glucose or oligosaccharides of glucose.

The present invention also pertains to further but related amino sugars in pure form.

The compounds of the present invention are obtained from the materials produced by culturing a microorganism of the family Actinoplanaceae or by chemical or enzymatic hydrolysis of such material.

A microorganism of the family Actinoplanaceae and of the order Actinomycetales, preferably a strain of the genus Actinoplanes, such as Actinoplanes spec. SE 50 (CBS 961.70), SB 18 (CBS 957.70) and SE 82 (CBS 615.71), or mutants or variants thereof are thus cultured in a now known manner. Strains SE 50/13 (CBS 614.71) and SE 50/110 (CBS 674.73) have proved to be particularly suitable with regard to the total yield. The description of both strains corresponds largely to that of the parent strain SE 50 (CBS 971.60) from which these strains have been obtained by natural selection without using mutagens. A solid or liquid, especially liquid, aqueous nutrient media is used, with the addition of the usual sources of carbon, sources of nitrogen salts and antifoaming agents in customary concentrations. The carbon sources used are generally carbohydrates, especially starch, maltose, glucose and mixtures of two or three of these material complex mixtures, such as commercially available malt extract. The nitrogen sources include the customary complex mixtures, such as casein hydrolysate, yeast extract, peptone, fishmeal, fish solubles, corn steep liquor, meat extract and mixtures thereof, as well as amino acids and/or ammonium salts. The culture is carried out aerobically in aerated shaken flasks or in conventional culture containers.

As is known, the nature and concentration of the source of carbon, in combination with the particular strain used for the fermentation, influences the nature of the product. In nutrient solutions which contain more than 2 wt. % of starch, compounds containing a total of 4 to 8 hexose units are predominantly formed and use of the strain SE 50/13 (CBS 614.71) in particular favors this type of producton. Under certain circumstances, as little as 0.1 to 3 wt. % of starch in a nutrient solution which also contains adequate glucose (about 3.5 wt. %) will produce mixtures of several amino sugars having 4 to 8 hexose units.Such conditions yield the higher compounds of the present invention which are suitable as starting materials for the lower members upon subsequent hydrolytic treatment.

On the other hand, use of starch-free nutrients, especially with the addition of maltose when using strain SE 50 (CBS 961.70), produces mixtures of compounds in which di- and trisaccharides predominate. Nutrient solutions which contan only glucose as the source of carbon have proved particularly suitable for preparation of material in which the compound in which R is one glucose residue predominates.

None of these conditions however produces a single compound to the exclusion of the other. If the nutrient solution contains excess glucose, the longer-chain compounds are also formed if the duration of fermentation is prolonged. This can be avoided, with certain limits, if exhaustion of the nitrogen sources coincides during fermentation with the exhaustion of glucose. On the other hand, if the glucose is dispensed with entirely in the nutrient solutions and maltose is added as the source of carbon, material in which the compound has two hexose units is obtained predominantly. The pure maltose can be replaced by cheaper material such as, for example, "Maltzin", a natural malt extract, and depending upon the content of maltotriose, the next-higher oligosaccharide material is also formed. The strain SE 50/110 (CBS 674.73) has proved to be particularly suitable for the preparation of material rich in the lower chain compounds containing 1, 2 or 3 glucose units. In optimal nutrient solutions, this strain produces a yield of lower chain material about twice that produced by SE 50/13 (CBS 614.71). Incubation temperatures generally lie between 15° and 45° C, preferably between 24° and 32° C. However longer chain material containing 4 to 8 glucose units are produced with SE 50 (CBS 961.70) and SE 50/13 (CBS 614.71) at a higher temperature, for example, 28° C. Shorter chain material containing 1, 2 or 3 glucose units are obtained using strains SE 50 (CBS) 961.70) and SE 50/110 (CBS 674.73) at a lower temperature, for example, 24° C. The duration of culture is generally 1 to 8 days, preferably 2 to 6 days and here again longer durations of culture, especially if an excess of carbohydrate is used, favor the formation of the longer chain materials.

The pH of the culture medium will range from 5.0 to 8.5, generally 6,0 to 7,8. The endpoint of the fermentation can be determined by determining the inhibitory activity content in an enzymatic inhibition test and by determing the composition by thin layer chromatography.

Material rich in the shorter chain compounds can be obtained from the longer chain material by chemical or enzymatic hydrolysis of monosaccharide units. Chemical hydrolysis is carried out in 1 to 5N aqueous mineral acid at 50° to 100° C., especially at 90° to 100° C., over a period of 10 to 180 minutes. Enzymatic hydrolysis is carried out by incubation with a suitable hydrolase, especially a β-amylase, an α-amylase of microbial origin such as from B. subtilis that is not inhibited by the compounds of the invention, or an amyloglucosidase. Hydrolysis can also be carried out microbially by culturing a suitable microorganism, for example, *Aspergillus niger* ATCC 11,394, in a nutrient medium containing 1 to 10% of the amino sugar as the sole carbon source.

The pure compounds of the present invention are obtained from the foregoing products of either the Actinomycetes culture broths or the hydrolysis.

The isolation, and purification, of the individual compounds of the invention thus starts either from microbiological culture broths or from acid hydrolysates or from incubation mixtures in which the enzymatic and/or microbiological restructuring or degradation of the higher members of the amino sugar derivatives has been carried out.

The longer chain material containing 4 to 8 glucose units is initially separated, after prior decolorizing and concentration of the solutions, by direct precipitation. This material is further processed as discussed hereafter.

The shorter chain compounds containing 1 to 3 glucose units are initially isolated by adsorption on active charcoal at the neutral pH, with subsequent desorption utilizing aqueous alcohols or acetone, especially 50 to 80% strength acetone. The desorption can be carried out completely at acidic pH values in the range of pH 1.5 to 4, preferably pH 2 to 3. If the starting solutions are very dark in color, they are decolorized prior to the adsorption by means of active charcoal, utilizing acidic pH values (pH 1 to 3), or with nonspecific adsorption resins, for example, Lewapol CA 9221/0.35 mm particle size (Bayer AG) in a pH range of 2 to 7, preferably 2 to 3. The active charcoal preferentially binds colored material in the acid range only, while Lewapol does not adsorb the amino sugar derivatives either at neutrality or in the acid range.

In order to separate the pure compounds of the present invention, their weakly basic character can be utilized. Under suitable conditions, namely a pH 1 to 8, preferably pH 2 to 4, and at low ionic strength corresponding to a conductivity of less than 10 mS.cm$^{-1}$, preferably less than 2 mS.cm$^{-1}$, the compounds are bound by strongly acid cation exchanges, such as for example, Dowex 50 W (Dow Chemicals) in the protonated form. The compounds can be bound particularly successfully from an acetone solution (50% to 80% acetone, pH 1 to 5, preferably 2 to 4) to cation exchangers, which, under these conditions, exhibit a substantially enhanced adsorptive capacity for the compounds. If the solution contains more than 50% of acetone, it is also possible to bind the compounds to weakly acid exchangers such as Amberlite IRC-50 (protonated form).

Aqueous solutions of acids or bases, preferably ammonia or hydrochloric acid, particularly in concentrations of 0.01 to 1 Eg./L, are best used for desorbing the compounds of the invention from the cation exchangers.

The desorbates are neutralized with a weak acidic or basic ion exchanger, or the base acid is stripped from the desorbates in vacuo, and the compounds are obtained, after concentration of the solution, by lyophilization or by precipitation with organic solvents such as 10 to 20 volumes of acetone.

Furthermore, it has proved possible to separate the lowmolecular compounds of the present invention from inert saccharides by chromatography on exchangers based on cellulose, preferably phospho-cellulose (Serva, Heidelberg). Buffers, preferably phosphate buffers, of low ionic strength, preferably 2 to 10 mM and especially 5 to 10 mM, and having a pH in the range of 2.5 to 8, preferably at pH 5 to 6, are used as running agents. A prerequisite for effective fractionation is that the salt contents in the preparation to be fractionated should be as low as possible.

To prepare the individual compounds of the present invention in a pure state, the pre-purified preparations, prepared as described above, are chromatographed using a suitable molecular sieve, such as for example, Bio-Gel P-2 (Bio-Rad, Munich). Fractions of the eluate are examined by thin layer chromatography and those which contain the pure compounds of the present invention are combined, re-chromatographed and finally lyophilized after concentration, or precipitated by means of organic solvents, as described above.

The compounds of the present invention are, chemically, carbohydrates. They form a series of which the amino sugar derivative [$C_{19}H_{33}O_{13}N$] is to be regarded as the initial member; i.e. R is a single glucose residue. The remaining compounds can be deemed to be higher members of this series, successively having one or two additional units of glucose. All members of this series are characterized in that upon total acid hydrolysis, "component I" [$C_{13}H_{19}O_7N$] and glucose are formed. "Component I" has been shown to have the structural formula:

"Component I"

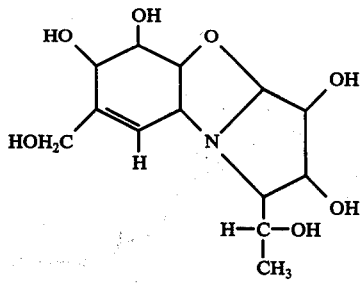

This compound, which itself has a strong anti-hyperglycemic action, is the subject of copending U.S. application Ser. No. 506,549, filed Sept. 16, 1974.

The initial member base substance of the series of the present invention has one glucose unit. This compound is a colorless, amorphous solid of good solubility in water, dimethylformamide, dimethylsulfoxide, methanol and hot ethanol. On thinlayer chromatography using 10:6:4 (v/v) ethyl acetate:methanol: water, the compound shows an Rf value of 0.46 (maltose = 0.50 and glucose = 0.65) on F 1500 silica gel films (Schleicher & Schüll) and of 0.47 (maltose = 0.54 and glucose = 0.66) on F 254 silica gel plates (Merck, Darmstadt). A brown-black coloration is obtained at room temperature or after slight warming upon application of silver nitrate/sodium hydroxide spray reagent.

This compound is silylated (together with α- and β-D-glucose or sucrose as the internal standard) in a mixture of pyridine (1), trimethylchlorosilane (0.5) and N-methyl-trimethyl-silyltrifluoroacetamide (1) and subjected to gas chromatography in a 6 ft. glass column filled with 3% SE 30 silicon-elastomer (Hewlett Packard) on Chromosorb WAW. The injection and detector temperature is 300° C. The oven temperature is 220° C, isothermal, until elution of α- and β-D-glucose standards with subsequent temperature increases at the rate of 15° C/minute up to 300° C. A flame ionization detector is employed with nitrogen as the carrier gas being fed at 40 ml/minute and air as the combustion gas at 80 ml/minute and hydrogen at 20 ml/minute. The compound showed a retention time of 16–17 minutes (α-D-glucose = 3 minutes, β-D-glucose = 4 minutes, and sucrose = 12–13 minutes).

A non-crystalline sample of the compound (obtained by concentrating a methanol solution) dissolved in water showed a specific optical rotation, $[\alpha]_D$, of +134.3°.

The IR spectrum in potassium bromide is poor and rather inconclusive, main absorption band being in the O—H and C—O areas.

The NMR spectrum in CD$_3$OD at 220 MHz is shown in FIG. 1 (Abscissa = δ ppm). Predominant features are shown in Table I which follows:

Table I

| In ppm | Multiplicity | Relative Intensity | |
|---|---|---|---|
| 1.3 | Doublet; J = 6.5 Hz | 3 H | |
| 2.3 | "Triplet", J$_1$ and J$_2$ 8–10 Hz | 1 H | |
| 3.15 | "Triplet"; J$_1$ and J$_2$ 7–9 Hz | 1 H | |
| 3.3 – 3.9 | Signals cannot be allotted individually | 12 H | |
| 4.13 | AB system; J = 12 Hz | 2 H | |
| (4.48 and | Doublet; J = 7 Hz) | 1 H | |
| (5.1 | Doublet; J = 2.5 Hz) | | |
| 4.9 | Singlet | 11 H | protons replaced by deuterium |
| 5.0 | Doublet; J = 2–3 Hz (poor resolution) | 1 H | |
| 5.8 | Doublet; J = 3–4 Hz (poor resolution) | 1 H | |
| | | 33 H | |

When this compound is reacted in 1:1 acetic anhydride: pyridine at room temperature, a decaacetyl derivative (m.w. 903) is obtained. The NMR spectrum of the decaacetyl derivative is shown in FIG. 2. If carried out in 1:1 glacial acetic acid: acetic anhydride with catalytic amounts of sulfuric acid, the formation of an undecaacetyl derivative (m.w. 945) in addition to the decaacetyl derivative can be detected by mass spectroscopy. MS spectrum of the decaacetyl derivative shows a molecular peak at 903 (2.5% relative intensity) and a base peak at 843. Important fragment peaks in the upper mass range are 844 (55% relative intensity), 784 (36% relative intensity), 783 (34% relative intensity), 759 (34% relative intensity), 556 (36% relative intensity), 496 (37% relative intensity) and 436 (29% relative intensity).

Methylation with methyliodide/sodium hydride in dimethylsulfoxide by the method of Hakomori yield a decamethyl derivative as the main product, together with a undecamethyl derivative in small amounts. The mass spectrum shows a molecular peak at 623 (6.1% relative intensity) with a base peak at 535. A second molecular peak is observed at 637 (0.2% relative intensity).

Spectroscopic data and chemical properties show the following structure for this compound.

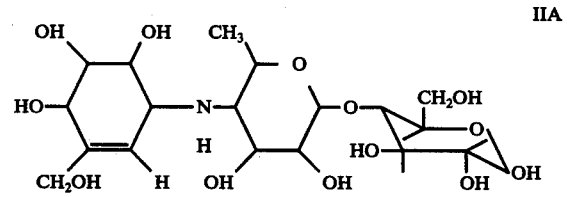

IIA

More particularly the NMR spectra demonstrates that the initial member is the compound O-{4,6-bis-desoxy-4-[1 S-(1,4,6/5)-4,5,6-trihydroxy-3-hydroxymethylcyclohex-2-en-1-ylamino]-α-D-glucopyranosyl}-

(1→4)-D-glucopyranose of the conformational structural formula:

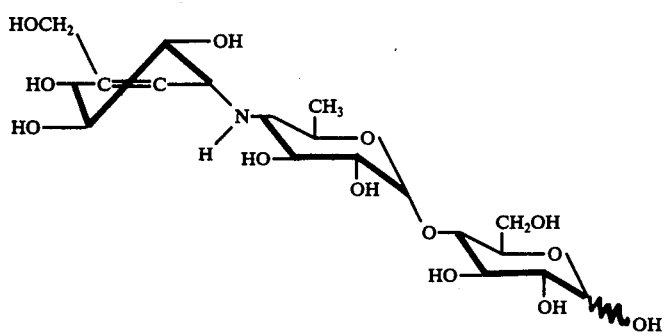

IIb

The next member of the series has the formula $C_{25}H_{43}O_{18}N$ and is readily water-soluble amorphous solid product. On thin layer chromatography it demonstrates an Rf value of 0.35 on F 1500 silica gel films and 0.33 on F 254 silica gel plates using the system described above.

The compound has a rather inconclusive IR spectrum, of poor resolution, with main absorption bands again being in the range of the O—H and C—O valency vibrations (3,700–3,100 cm$^{-1}$ and 1,180–950 cm$^{-1}$, respectively). Its optical rotation in water, $[\alpha]_d$ is $+147.2°$. Its NMR spectrum in $D_2O$ at 220 MH$_z$ is shown in FIG. 3.

Methylation as above produces a compound methylated 13-fold, and small amounts of a product methylated 14-fold. The mass spectrum of the methylation product shows the molecular peak at 827 (1.5% relative intensity) corresponds to an empirical formula $C_{38}H_{69}NO_{18}$.

A second molecular peak of 0.1% relative intensity is present at 841. The most important fragment peaks are:

739 (27% relative intensity), 592 (3.7% relative intensity), 535 (30% relative intensity), 388 (9% relative intensity), 386 (13% relative intensity), 284 (13% relative intensity), 187 (12% relative intensity), 171 (40% relative intensity), 101 (34% relative intensity) and 88 (25% relative intensity) with a base peak of 75.

Chemical and spectroscopic properties show the following structure for this compound:

IIIA

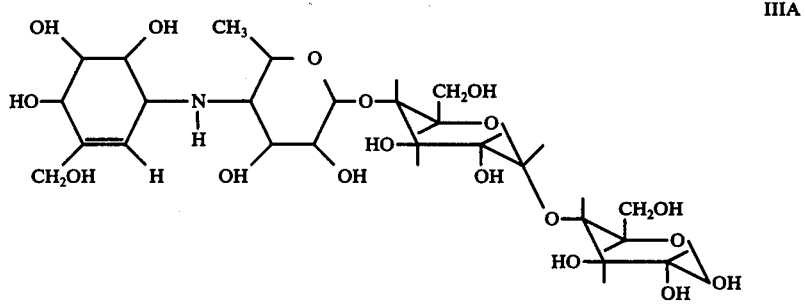

More particularly, the second member of this series is the compound O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl-(1→4)-D-glucopyranose of the conformational structural formula:

IIIB

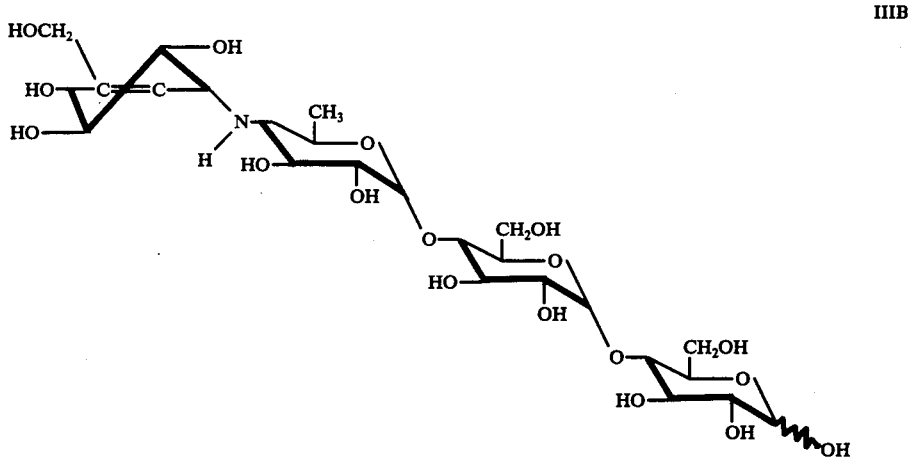

The next higher member of the series is obtained in lower than expected yields with an isomeric compound being predominantly formed. On acid partial hydrolysis, both these compounds can be split to give the first member of the series and glucose in the molar ratio of 1:2.

The material present in lower amounts is the compound O-{4,6-bisdesoxy-4-[1 S-(1,4,6/5)-4,5,6-trihydroxy-3-hydroxymethylcyclohex-2-en-1-ylamino]-α-D-glucopyranosyl}-(1→4)-O-α-D-glucopyranosyl-(1→4)-O-α-D-glucopyranosyl-(1→4)-D-glycopyranose of the conformational structural formula:

These isomers show $R_{glucose}$ values of 0.41 to 0.46 on F 1500 plates using 50:30:20 n-butanol:ethanol:water. The presence of the isomer having the structure shown in Formula V can be shown by analysis of the products of hydrogenolytic degradation using palladium on charcoal. The products of this degradation thus include 3-hydroxymethyl-4,5,6-trihydroxy-4-O-α-D-glucopyransyl-(1)-hexane, O-(4-amino-4,6-bisdesoxy-α-D-glucopyranosyl)-(1→4)-O-α-D-glucopyranosyl-(1→4)

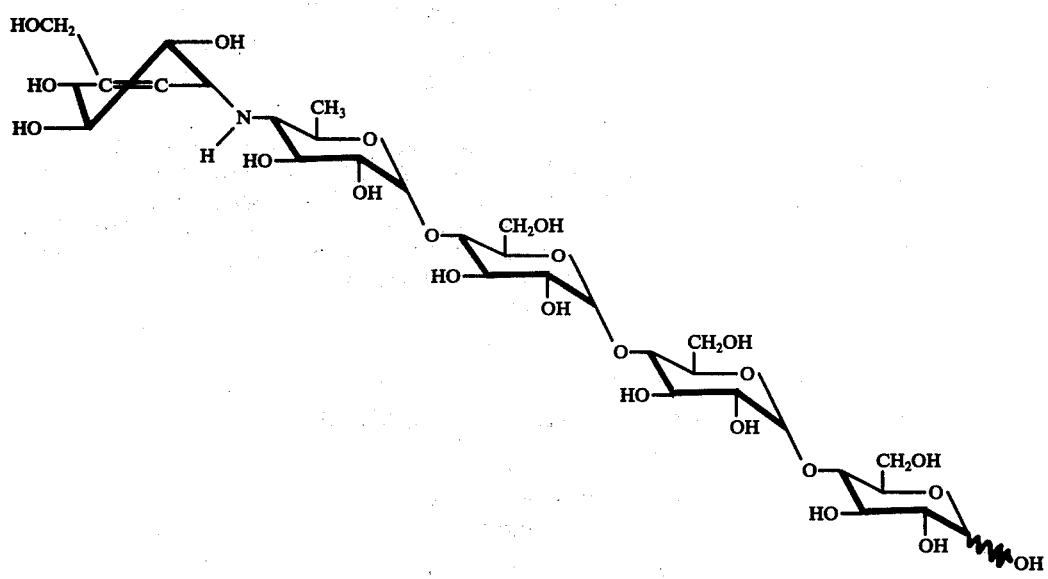

IV

The isomeric material present in larger amounts is the compound O-{4,6-bisdesoxy-4-[1 S-(1,4,6/5)-4,5,6-trihydroxy-3-hydroxymethyl-4-O-α-D-glucopyranosyl-(1→4)-cyclohex-2-en-1-ylamino]-α-D-glycopyranosyl}-(1→4)-O-α-D-glucopyranosyl-(1→4)-D-glucopyranose of the conformational structural formula:

-D-glucopyranose, and glucose. Since the hydrogenation reduces the double bond of the hexene group and cleaves the amino bond, it is clear this compound, which is isomeric to the compound of Formula IV is structurally related to the compound of Formula IIIA or IIIB characterized however by the presence of a further glucopyranosyl group in the 4-position of the cyclohexene ring.

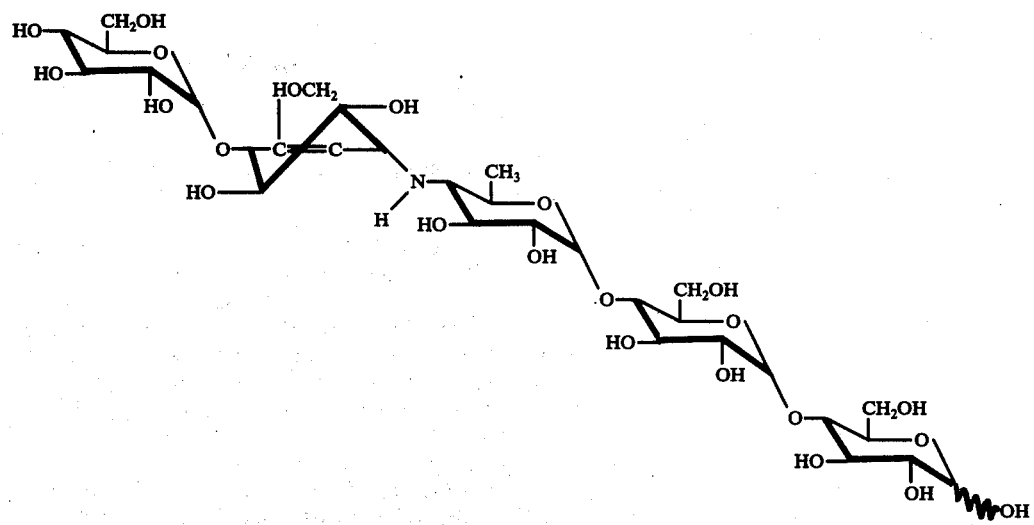

V

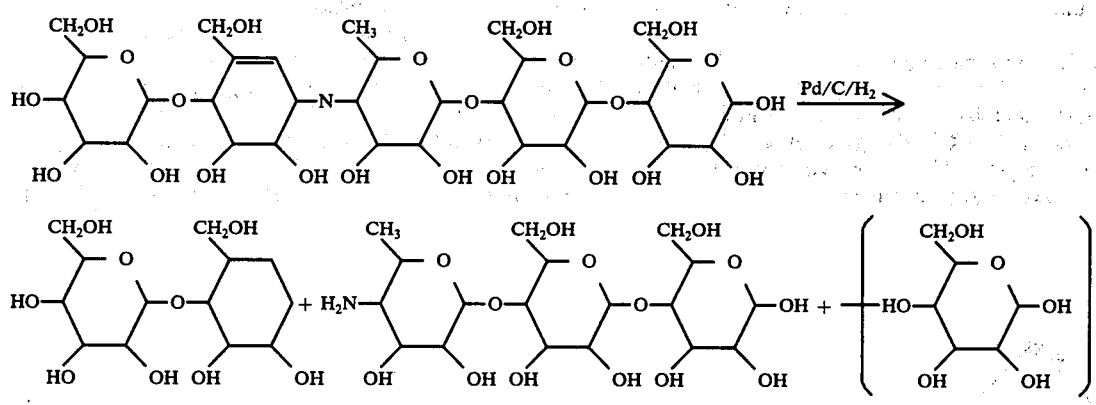

The presence of the isomer having the structure shown in formula IV is demonstrated by the formation of validatol (S. Horii et al., Journal of Antibiotics XXIV, 59 (1971)) and O-(4-amino-4,6-bisdesoxy-α-D-glucopyranosyl)-(1→4)-O-α-D-glucopyranosyl-(1→4)-O-α-D-glucopyranosyl-(1→4)-D-glucopyranose.

1:8, (the percentages of glucose being 74.4%, 79.7%, 83.3%, 86.5% and 89.1%, respectively).

Upon thin layer chromatography using F 1500 silica gel plates with 45:35:20 n-butanol:ethanol:water as the solvent, the following $R_f$ values are observed upon threefold development:

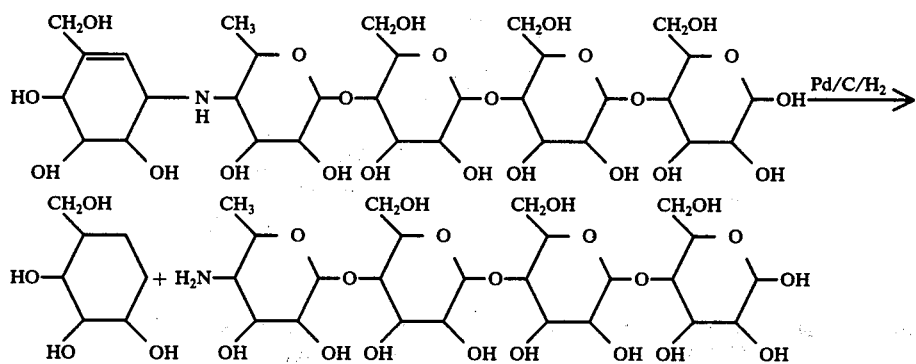

In a second experiment the isomers with 3 glucose units were methylated according to well known methods, hydrolysed, reduced with sodium borohydride, acetylated and analyzed by gas chromatography. Wereas the compound with formula IV yields only 1,4,5-tri-O-acetyl-2,3,6-tri-O-methyl-D-glucitol, the compound with formula V yields 1,4,5-tri-O-acetyl-2,3,6-tri-O-methyl-D-glucitol and 1,5-di-O-acetyl-2,3,4,6-tetra-O-methyl-D-glucitol in a molar ratio of 2:1.

The isomeric compounds with formulas IV and V were separated by chromatography on a acidic ion exchange resin with 0.025 N hydrochloric acid as an eluant.

The higher members of the series containing 4 to 8 glucose units with molecular wights of from 969 to 1617 are less active saccharase inhibitors although in vitro their α-amylase inhibition is higher. On acid hydrolysis of these higher members, the lower components can, in each case, be detected as intermediate products together with glucose and maltose. Thin layer chromatography using 50:30:20 n-butanol:ethanol:water, on F 1500 silica gel plates give $R_{glucose}$ values of 0.30–0.34 (predominantly four glucose units); 0.21–0.23 (predominantly five glucose units); 0.14–0.16 (predominantly six glucose units); and 0.09–0.11 (predominantly seven glucose units).

As in the case of the lower members of this series, total acid hydrolysis yields "Component I" and glucose in discrete molar ratios, specifically 1:4, 1:5, 1:6, 1:7 and

| Ratio Glucose:Compound I | Standard | $R_f$ value |
|---|---|---|
|  | Glucose | 0.77 |
|  | Maltose | 0.65 |
|  | Maltotriose | 0.51 |
|  | Maltotetraose | 0.39 |
|  | Maltopentaose | 0.27 |
| 4:1 |  | 0.25 |
|  | Maltohexaose | 0.21 |
| 5:1 |  | 0.18 |
|  | Maltoheptaose | 0.15 |
| 6:1 |  | 0.13 |
|  | Maltooctaose | 0.11 |
| 7:1 |  | 0.09 |
| 8:1 |  | 0.07 |

Similarly, catalytic hydrogenation as discussed above demonstrates that some but not all of the glucose units of these higher members are bound through the 4-position of the cyclohexene group.

Since these compounds contain oligoglucosidic linear chains with 1→4 linkages, they can serve as substrates for certain carbohydrate degrading enzymes. The range of enzymes is obviously limited to those which are not substantially inhibited by the compounds. Bacterial and fungal α-amylases can be used to degrade any oligoglucosidic chain containing 2 or more glucose units and yielding compounds of lower molecular weight and inert saccharide fragments such as maltose and maltotriose. This degradation procedure is further proof for 1→4 α-linkage. Compounds of the invention containing 4 to 8 glucose units are also degradable to some extent by β-amylase. Since β-amylase splits off maltose units from the non-reducing end of a glucose chain having 1→4 α-linkages, careful analysis of β-amylase degradation products yields valuable information on any oligo-glucosidic substituent bound to the 4-position of the cyclohexene ring, specifically its chain length, and the number of glucoses in the chain attached to the bis-desoxyglucose; i.e., the reducing end of the compound. The compounds containing 4, 5, 6, 7 or 8 glucose units are however not completely degradable by β-amylase, the resistance of some fragment of the compound apparently being due to insufficient structural requirements for β-amylase attack.

The results of β-amylase degradation can be summarized as follows:

| No. of glucose units in starting material | No. of glucose units in degradation product(s) | Maltose units removed |
| --- | --- | --- |
| 4 | 4 | 0 |
|   | 2 | 1 |
| 5 | 5 | 0 |
|   | 3 | 1 |
| 6 | 6 | 0 |
|   | 4 | 1 |
|   | 2 | 2 |
| 7 | 7 | 0 |
|   | 5 | 1 |
|   | 3 | 2 |
| 8 | 8 | 0 |
|   | 6 | 1 |
|   | 4 | 2 |
|   | 2 | 3 |

In each case some starting material, possibly isomeric, is recovered. As to that material which is degraded, it should again be emphasized that the β-amylase will successively remove only maltose units and only from the non-reducing end of the oligosaccharide. Consequently while not wishing to be bound by any theory and while the precise structure of these higher compounds has not been fully elucidated, it appears the compounds containing 4, 5, 6, 7 and 8 glucose units include derivatives of the lower members of Formula IIIA and IIIB containing chains of 2,3,4,5 and 6 glucose units joined 1→4 α to each other with the last being joined 1α to the 4-position of the cyclohexene ring.

Methylation of the compounds with methyliodide/sodium hydride in dimethyl sulfoxide, subsequent total hydrolysis and derivatization, followed by gas chromatographic analysis yields only the 2, 3, 6-trimethyl glucose derivative, so that the glucose units are necessarily joined 1 →4 in an exclusively linear structure. A second methylation product, which is found to a varying degree or under certain circumstances not at all, is the 2,3,4,6-tetramethyl derivative. The existence of this derivative and its molar ratio to the trimethyl derivative is dependent on the substituent attached to the cyclohexane ring.

Each of these isomeric forms; i.e. those of Formula I wherein R is an oligosaccharide unit of 4 to 8 glucose units and those wherein one or more of these glucose units are bound to the 4-position of the cyclohexane ring is embraced by the present invention. Both groups can thus be depicted by the formula:

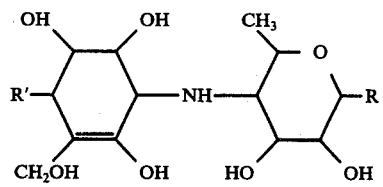

where R' is hydroxy, or one to seven glucose residues and R is one to eight glucose residues, the total of glucose residues embraced by R' and R being from 4 to 8.

As noted above, these compounds are inhibitors of glycoside-hydrolases and can thus be used in conditions in which inhibition of such emzymes is desirable.

It is known that in animals and man, hyperglycaemias occur after ingestion of foodstuffs and beverages containing carbohydrates (for example cereal starch, potato starch, fruit, fruit juice, beer or chocolate). These hyperglycaemias are due to a rapid degradation of the carbohydrates by glycoside-hydrolases (for example salivary and pancreatic amylases, maltases and saccharases) in accordance with the following equation:

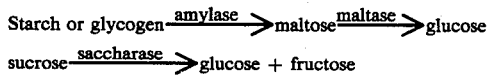

These hyperglycaemias are particularly pronounced and long-lasting in the case of diabetics. With adipose subjects, alimentary hyperglycaemia frequently leads to a particularly powerful secretion of insulin which in turn leads to increased fat synthesis and reduced fat degradation. Following such hyperglycaemias, hypoglycaemia frequently occurs, due to the insulin secretion, both in metabolically sound and in adipose persons. It is known that both hypoglycaemias and chyme remaining in the stomach promote the production of gastric juice which in turn initiates or favors the development of gastritis or of gastric or duodenal ulcers.

The inhibitors of glycoside-hydrolases according to the invention, obtained and isolated in accordance with the presently described methods, substantially reduce alimentary hyperglycaemia, hyperinsulinaemia and hypoglycaemia. This can be observed after feeding rats and/or humans with starch, sucrose or maltose. The compounds accelerate the passage of carbohydrates through the stomach and also inhibit the absorption of glucose from the intestine. The conversion of carbohydrates into lipids of the fatty tissue and the incorporation of alimentary fat into the fatty tissue depots is accordingly reduced or delayed.

It is also known that carbohydrates, especially sucrose, are split by microorganisms in the mouth cavity and that this encourages caries formation. The present inhibitors can be used to prevent or reduce such action.

The following describes the inhibitory profile of the present compounds.

In vitro amylase test

One amylase inhibitor unit (1 AIU) is defined as the amount of inhibitor which inhibits two amylase units to the extent of 50%. One amylase unit (AU) is the amount of enzyme which under the test conditions specified below splits 1 μequivalent of glucoside bonds in the starch per minute. The μequivalents of split bonds are determined colorimetrically as μequivalents of reducing sugars formed, using dinitrosalicylic acid, and are quoted as $\mu$equivalents of maltose equivalents, using a maltose calibration curve. To carry out the test, 0.1 ml of amylase solution (20-22 AU/ml) are mixed with 0-10 $\mu$g of inhibitor or 0-20 $\mu$l of the solution to be tested in 0.4 ml of 0.02 M sodium glycerophosphate buffer/0.001 M CaCl$_2$, pH 6.9, and the mixture is equilibrated for 10-20 minutes in a water bath at 35° C. The mixture is then incubated for 5 minutes at 35° C with 0.5 ml of a 1% strength starch solution which has been pre-warmed to 35° C (soluble starch No. 1,252 from Merck, Darmstadt), and thereafter 1 ml of dinitrosalicyclic acid reagent (according to P. bernfeld in Colowick-Kaplan, Meth. Enzymol., Volume $l$, page 149) is added. To develop the color, the batch is heated for 5 minutes on a boiling water bath and then cooled, and 10 ml of distilled water are added. The extinction at 540 nm is measured against a correspondingly made-up blank without amylase. For evaluation, the amylase activity which is still effective after addition of inhibitor is read off a previously recorded amylase calibration curve and the percentage inhibition of the amylase employed is calculated therefrom. The percentage inhibition is plotted as a function of the quotient $$\frac{\mu g \text{ of inhibitor }^+}{AU^{++}}$$

$^+$ relative to solid
$^{++}$ AU in non-inhibited batch of the same series and the 50% inhibition point is read off the curve and converted to AIU/mg of inhibitor.

In vitro saccharase test

One saccharase inhibitor unit (SIU) is defined as the amount of inhibitor which inhibits two saccharase units to the extent of 50%. One saccharase unit (SU) is the amount of enzyme which under the test conditions specified splits 1 $\mu$mol of sucrose to glucose and fructose per minute. The $\mu$mols of glucose formed are determined quantitatively by means of the glucose oxidase reaction under conditions under which a further splitting of the sucrose by the saccharase no longer takes place. To carry out the test, 0.05 ml of solubilized saccharase [from the mucous membrane of the small intestine of the pig, according to B. Borgastrom, A. Dahlquist, Acta Chem. Scand. 12, (1958), page 1,997], diluted with 0.1 M sodium maleate buffer of pH 6.0 to a SU content adjusted to 0.12 SU is mixed with 0-20 $\mu$g of inhibitor or 0-20 $\mu$l of the solution to be tested and brought up to 0.1 ml with 0.1 M sodium maleate buffer of pH 6.0. The mixture is equilibrated for 10 minutes at 35° C and 0.1 ml of an 0.05 M sucrose solution in 0.1 M sodium maleate buffer of pH 6.0, pre-warmed to 35° C, is then added. The mixture is incubated for 20 minutes at 35° C, the saccharase reaction is stopped by addition of 1 ml of glucose oxidase reagent, and the incubation is continued for a further 30 minutes at 35° C. (The glucose oxidase reagent is prepared by dissolving 2 mg of glucose oxidase, Boehringer, No. 15,423, in 100 ml of 0.565 M tris-HCl buffer of pH 7.0 and subsequently adding 1 ml of detergent solution (2 g of Triton X 100 + 8 g of 95% strength and analytical grade ethanol), 1 ml of dianisidine solution (260 mg of o-dianisidine. 2HCl in 20 ml of H$_2$O) and 0.5 ml of 0.1% strength aqueous peroxidase solution, Boehringer, No. 15,302). Thereafter, 1 ml of 50% strength H$_2$SO$_4$ is added and a measurement carried out at 545 nm against a corresponding blank. To evaluate the results, the percentage inhibition of the saccharase employed is calculated and converted to SIU/g of SIU/liter from the 50% inhibition point, using a glucose calibration curve.

In vitro maltase test

One maltase inhibitor unit (MIU) is defined as the amount of inhibitor which inhibits two maltase units to the extent of 50%. One maltase unit (MU) is the amount of enzyme which in one minute, under the test conditions specified below, splits 1 $\mu$mol of maltose into 2 $\mu$mol of glucose. The $\mu$mol of glucose formed are determined quantitatively by means of the glucose oxidase reaction under conditions such that further splitting of maltose by the maltase no longer takes place. To carry out the test, 0.05 ml of solubilized maltase [from the mucous membrane of the small intestine of the pig, according to B. Borgstrom, A, Dahlquist, Acta Chem, Scan. 12, (1958), page 1,997], diluted with 0.1 M sodium maleate buffer of pH 6.0 to 0.060-0.070 MU is mixed with 0-20 $\mu$g of inhibitor of 0-20 $\mu$l of the solution to be tested and made up to 0.1 ml with 0.1 M sodium maleate buffer of pH 6.0. The mixture is equilibrated for 10 minutes at 35° C and 0.1 ml of an 0.05 M maltose solution in 0.1 M sodium maleate buffer of pH 6.0, pre-warmed to 35° C, is then added. The mixture is incubated for 20 minutes at 35° C and the maltase reaction is stopped by addition of 1 ml of the glucose oxidase reagent described above, and the incubation is continued for a further 30 minutes at 35° C. Thereafter, 1 ml of 50% strength sulfuric acid is added and a measurement carried out at 545 nm against a corresponding blank.

To evaluate the results, the percentage inhibition of the maltase employed is calculated and converted to MIU/g or MIU/liter from the 50% inhibition point, using a glucose calibration curve.

The results of the in vitro enzyme inhibition tests for specific individual compounds and discrete ranges of higher members of the compounds of the present invention in which R is one or more glucose residues are summarized in Table II which follows:

Table II

| Formula | Number of Glucose Units | $\alpha$-Amylase Inhibition AIU/g | Saccharase Inhibition SIU/g | Maltase Inhibition MIU/g |
|---------|------------------------|-----------------------------------|-----------------------------|--------------------------|
| II B    | 1                      | 300,000                           | 30,000                      | 5,000                    |
| III B   | 2                      | 300,000                           | 68,000                      | 15,000                   |
| V       | 3                      | 1,400,000                         | 21,000                      | 5,000                    |
|         | 4-6                    | 17,500,000                        | 8,500                       | —                        |
|         | 5-7                    | 30,000,000                        | 2,500                       | —                        |

As can be seen from the above, the specific in vitro inhibitory activity towards pancreas-$\alpha$-amylase increases greatly with increasing molecular weight in the series; thus, the compounds with 5 to 7 glucose units show a 100-fold greater inhibition in vitro than does the compound with 1 or 2 units. Saccharase inhibition is most pronounced for the derivative having two units, the derivative having one glucose unit showing inhibition only half as much, and the higher member showing further decreases in saccharase inhibition.

In vivo, the activity in saccharase inhibition (the sucrose overfeeding test) run approximately parallel to the specific inhibitory activity found in vitro. On the other hand, in vivo starch digestion (the starch feeding test) for the compounds having 1, 2 or 3 glucose units unexpectedly increases 10 to 40-fold in comparison to the amylase inhibition in vitro. The significance of this will be seen from the following.

The produce an alimentary hyperglycemia and hyperinsulinaemia, groups of 6 fasting rats are given (a) 2.5 g of sucrose, (b) 2.5 g of maltose or (c) 1 g of boiled starch orally, in aqueous solution or suspension. Six other rats are given the same carbohydrates in the same amount and a glycoside hydrolase inhibitor in the amount indicated. In addition, six other rats are given an appropriate volume of saline. The blood glucose and the serum insulin are then measured at short intervals of time, in the blood from the retro-orbital venous plexus. Blood glucose determinations are carried out in the Auto-Analyser device (Technicon), according to Hoffmann: J. biol. Chem. 120, 51 (1937), or enzymatically by means of glucose oxidase and o-dianisidine hydrochloride and the serum insulin determinations are carried out according to the method of Hales and Randle: Biochem. J. 88, 137 (1963).

The results for in vivo saccharase inhibition (administration of sucrose) in the fasting rat are shown in Table III which follows:

As can be seen from the above, in vivo activity in saccharase inhibition parallels that observed in vitro. Thus the observed $ED_{50}$ increases as saccharase inhibition units per milligram decreases. These are summarized in Table IV as follows:

Table IV

| Formula | Glucose units | Saccharase Inhibition In Vitro SIU/mg | In Vitro ($ED_{50}$ mg/kg) |
|---|---|---|---|
| IIB | (1) | 30 | 3.0 |
| IIIB | (2) | 68 | .21 |
| V | (3) | 21 | 2.65 |
| — | (4–6) | 8.5 | ~ 15.30 |
| — | (5–7) | 2.5 | ~ 52.00 |

Surprisingly the in vivo inhibition of starch digestion by the compounds of Formulas IIB, IIIB and V is much higher than would be expected from the in vitro amylase inhibition data and does not follow the anticipated pattern. In vivo data in the fasting rat following administration of starch, determined as described above, are presented in Table V which follows.

Table III

| Formula | n | Dose (SIU) | Blood Glucose in mg% (Mean ± SD) | | | |
|---|---|---|---|---|---|---|
| | | | 15 Min. | 30 Min. | 45 Min. | 60 Min. |
| | | Saline | 69 ± 5.2 | 84 ± 3.9 | 91 ± 5.9 | — |
| | | sucrose (control) | 117 ± 11 | 135 ± 8.1 | 152 ± 18 | — |
| IIB | 1 | sucrose + 50 SIU | 105 ± 11 | 123 ± 5.2* | 128 ± 11* | — |
| | | sucrose + 100 SIU | 89 ± 6.5*** | 111 ± 4.1*** | 116 ± 3.9*** | — |
| | | sucrose + 200 SIU | 72 ± 4.6*** | 95 ± 9.1*** | 104 ± 9.6*** | — |
| | | saline | 55 ± 4.5 | 92 ± 8.5 | 95 ± 6.4 | — |
| | | sucrose (control) | 113 ± 9.9 | 126 ± 20 | 127 ± 14 | — |
| IIIB | 2 | sucrose + 25 SIU | 71 ± 3.7*** | 100 ± 7.3* | 107 ± 2.4** | — |
| | | sucrose + 100 SIU | 58 ± 5.9*** | 92 ± 4.0** | 98 ± 5.0*** | — |
| | | saline | 66 ± 4.6 | 73 ± 4.3 | 76 ± 3.9 | — |
| V | 3 | sucrose (control) | 122 ± 6.6 | 125 ± 16.0 | 128 ± 14.8 | — |
| | | sucrose + 25 SIU | 88 ± 11.4** | 101 ± 12.0* | 104 ± 7.4** | — |
| | | sucrose + 50 SIU | 91 ± 9.4** | 106 ± 7.0* | 94 ± 9.0*** | — |
| | | sucrose + 100 SIU | 81 ± 7.2** | 90 ± 8.0*** | 97 ± 1.6*** | — |
| | | saline | 58 ± 2.9 | 49 ± 3.3 | 54 ± 4.8 | 63 ± 5.0 |
| | | sucrose (control) | 107 ± 11 | 121 ± 6.0 | 132 ± 16 | 132 ± 6.7 |
| — | 4–6 | sucrose + 25 SIU | 109 ± 6.4 | 105 ± 10** | 112 ± 9.1* | 108 ± 8.1*** |
| | | sucrose + 50 SIU | 103 ± 4.1 | 107 ± 15** | 102 ± 7.7** | 101 ± 9.2*** |
| | | sucrose + 100 SIU | 85 ± 8.1** | 94 ± 9.9*** | 95 ± 8.5*** | 85 ± 6.4*** |
| | | saline | 58 ± 2.9 | 49 ± 3.3 | 54 ± 4.8 | 63 ± 5.0 |
| | | sucrose (control) | 107 ± 11 | 121 ± 6.0 | 132 ± 16 | 132 ± 6.7 |
| — | 5–7 | sucrose + 75 SIU | 102 ± 11 | 108 ± 9.6* | 109 ± 7.5** | 101 ± 7.9** |
| | | sucrose + 150 SIU | 92 ± 7.0* | 100 ± 8.3*** | 109 ± 3.7** | 102 ± 6.3*** |
| | | sucrose + 300 SIU | 95 ± 8.1* | 84 ± 8.7*** | 93 ± 9.0*** | 91 ± 4.5*** |

*= Probability against sucrose (control) = < 0.05
**= Probability against sucrose (control) = < 0.01
***= Probability against sucrose (control) = < 0.001

Table V

| Formula | Gluc. Units | Dose (AIU) | Blood Glucose in mg% (Mean ± SD) | | | | | |
|---|---|---|---|---|---|---|---|---|
| | | | 5 Min. | 10 Min. | 15 Min. | 20 Min. | 30 Min. | 45 Min. |
| | | saline | 74 ± 6.2 | 74 ± 3.0 | 82 ± 9.4 | 71 ± 11 | 76 ± 5.4 | 90 ± 9.2 |
| | | starch (control) | 101 ± 8.8 | 135 ± 13 | 146 ± 4.8 | 151 ± 9.5 | 148 ± 18 | 156 ± 19 |
| IIB | 1 | starch + 75 AIU | 102 ± 2.9 | 130 ± 6.9 | 128 ± 5.4*** | 143 ± 11 | 125 ± 11* | 132 ± 18* |
| | | starch + 150 AIU | 98 ± 8.7 | 116 ± 9.0* | 128 ± 5.8*** | 127 ± 4.8*** | 115 ± 5.2** | 137 ± 5.2** |
| | | starch + 300 AIU | 87 ± 13 | 106 ± 1.8*** | 110 ± 8.9*** | 111 ± 2.1*** | 108 ± 5.3* | 121 ± 7.2* |
| | | saline | 61 ± 3.7 | 68 ± 3.9 | 83 ± 5.3 | 75 ± 8.7 | 91 ± 5.2 | 84 ± 1.5 |
| | | starch (control) | 85 ± 7.9 | 120 ± 7.7 | 132 ± 11 | 140 ± 12 | 135 ± 5.0 | 128 ± 14 |
| IIIB | 2 | starch + 150 AIU | 82 ± 7.5 | 105 ± 4.2** | 120 ± 6.0* | 124 ± 7.0* | 134 ± 6.1 | 125 ± 5.2 |
| | | starch + 300 AIU | 79 ± 8.2 | 97 ± 2.7*** | 105 ± 10** | 118 ± 6.7** | 119 ± 9.9** | 130 ± 5.9 |
| | | starch + 600 AIU | 70 ± 4.6 | 80 ± 8.8 | 94 ± 6.9 | 91 ± 16 | 103 ± 9.2 | 102 ± 4.2 |
| | | starch + 1,200 AIU | 70 ± 7.0*** | 84 ± 7.7*** | 88 ± 7.4*** | 97 ± 5.2*** | 97 ± 5.0*** | 100 ± 4.3*** |
| | | saline | 52 ± 2.3 | 75 ± 7.9 | 57 ± 3.7 | 78 ± 9.6 | 82 ± 6.5 | 70 ± 6.9 |
| | | starch (control) | 93 ± 7.3 | 133 ± 12 | 127 ± 9.3 | 152 ± 15 | 156 ± 15 | 124 ± 7.7 |
| V | 3 | starch + 750 AIU | 86 ± 8.5 | 107 ± 5.0*** | 117 ± 8.7* | 121 ± 12** | 126 ± 11*** | 114 ± 3.6*** |
| | | starch + 1,500 AIU | 77 ± 14* | 92 ± 9.6*** | 94 ± 9.5*** | 113 ± 9.7*** | 112 ± 8.8*** | 111 ± 4.2** |
| | | starch + 3,000 AIU | 65 ± 5.6*** | 101 ± 3.3*** | 82 ± 11*** | 112 ± 4.5*** | 109 ± 6.4*** | 104 ± 2.5*** |
| | | saline | — | 55 ± 4.8 | 63 ± 5.9 | 67 ± 5.8 | 72 ± 4.7 | 66 ± 5.0 |
| | | starch (control) | — | 103 ± 11 | 117 ± 8.6 | 118 ± 8.5 | 128 ± 8.9 | 109 ± 11 |
| — | 4–6 | starch + 6.000 AIU | — | 99 ± 4.5 | 118 ± 5.8 | 104 ± 8.1* | 123 ± 11 | 107 ± 7.3 |
| | | starch + 12.000 AIU | — | 90 ± 5.2* | 98 ± 8.2** | 99 ± 4.1*** | 117 ± 6.7* | 104 ± 8.2 |
| | | starch + 24.000 AIU | — | 74 ± 5.5*** | 82 ± 2.9*** | 83 ± 3.7*** | 96 ± 6.6*** | 85 ± 6.4** |
| | | saline | — | 55 ± 4.8 | 63 ± 5.9 | 67 ± 5.8 | 72 ± 4.7 | 66 ± 5.0 |
| | | starch (control) | — | 103 ± 11 | 117 ± 8.6 | 118 ± 8.5 | 128 ± 8.9 | 109 ± 11 |
| — | 5–7 | starch + 6.000 AIU | — | 95 ± 4.3 | 107 ± 3.3* | 102 ± 5.5** | 111 ± 3.0** | 102 ± 6.7 |
| | | starch + 12.000 AIU | — | 87 ± 8.6* | 94 ± 8.8** | 89 ± 8.5*** | 98 ± 8.3*** | 91 ± 4.3** |
| | | starch + 24.000 AIU | — | 74 ± 8.9*** | 84 ± 7.2*** | 84 ± 6.9*** | 85 ± 6.5*** | 85 ± 4.9*** |

*= Probability against starch (control) = < 0.05
**= Probability against starch (control) = < 0.01
***= Probability against starch (control) = < 0.001

It will be observed from the foregoing that while the level of saccharase inhibition is a characteristic function of molecular weight, both in vitro and in vivo, and amylase inhibition is conversely a direct function of molecular weight in vitro, in vivo inhibition of starch digestion does not decrease with decreasing molecular weight but surprisingly remains constant. Thus even though in vitro amylase in inhibiting activity decreases with molecular weight, the $ED_{50}$'s for the present compounds are substantially the same as those of the higher members. This is summarized in Table VI which follows.

Table VI

| Formula | Glucose Units | α-Amylase Inhibition In Vitro AIU/mg | Starch Digestion Inhibition In Vivo ($ED_{50}$ mg/kg) |
|---|---|---|---|
| IIB | (1) | 300 | 0.76 |
| IIIB | (2) | 300 | 1.60 |
| V | (3) | 1,400 | 1.61 |
| — | (4–6) | 17,500 | 1.42 |
| — | (5–7) | 30,000 | 1.00 |

It is thus possible to achieve simultaneously inhibition of both sucrose- and starch digestion with the pure lower members and to do so at a precise, predictable and characteristic dosage level.

The compounds also appear to have an advantageous effect on glucose absorption, as can be seen from the following data in Table VII in fasting rats for the compound of Formula IIIB (n = 2).

Table VII

| Dose | Blood Glucose in mg% (Mean ± SD) | | |
|---|---|---|---|
| | 15 Min. | 30 Min. | 45 Min. |
| saline | 72 ± 4.6 | 78 ± 1.3 | 87 ± 6.8 |
| glucose (control) | 142 ± 12 | 142 ± 12 | 158 ± 19 |
| glucose + 30 mg | 135 ± 13 | 128 ± 5.5 | 132 ± 7.3 |
| glucose + 60 mg | 125 ± 13* | 118 ± 2.9** | 130 ± 9.0*** |

*= Probability against glucose (control) = < 0.05
**= Probability against glucose (control) = < 0.01

Purification of the mixture of higher members of this series results in further unexpected increases both in activity and in specificity. This can be seen from a comparison of the α-amylase and saccharase in vitro inhibition data given in Table II above with the data in Table VIII below for the purified compounds:

Table VIII

| Number of Glucose Units | α-Amylase Inhibition AIU/g | Saccharase Inhibition MIU/g |
|---|---|---|
| 4 | 67,000,000 | 7,000 |
| 5 | 57,000,000 | 3,500 |
| 6 | 42,000,000 | 1,200 |
| 7 | 24,000,000 | 60 |
| 8 | 5,000,000 | 10 |

The above results show the high activity as an α-amylase inhibitor of the compound having 4 glucose units. The compounds having 5 and 6 units also exhibit considerably higher specific inhibitor activities than found with any previous preparation. There is of course an obvious decrease in inhibitor activity with increasing molecular weight, as can be seen from the compounds having 7 and 8 glucose units although these still show considerable inhibition. In vitro saccharase inhibition appears to be an inverse function of molecular weight. The compound with 4 glucose units exhibits about 1/10 of the specific activity of the compound having two glucose units whereas the inhibitory activity of the compound with 8 glucose units is only marginal.

The compounds can be administered without dilution, as for example as a powder or in a gelatin sheath, or in combination with a carrier in a pharmaceutical composition.

Pharmaceutical compositions will contain a major or minor amount, e.g. 0.1% to 99.5%, preferably 0.5% to 95% of the inhibitor in combination with a pharmaceutically acceptable non-toxic, inert carrier, the carrier comprising one or more solid, semi-solid or liquid diluent, filler and/or formulation adjuvant which is non-toxic, inert and pharmaceutically acceptable. Such pharmaceutical compositions are preferably in dosage unit form; i.e., physically discrete units containing a predetermined amount of the inhibitor corresponding to a fraction or multiple of the dose which is calculated to produce the desired inhibition. The dosage units can contain one, two, three, four or more single doses or, alternatively, one half, third or fourth of a single dose. A single dose preferably contains an amount sufficient to produce the desired level of inhibition upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, and the nature and gravity of the clinical condition, generally the dosage will be from about 30 to about $3 \times 10^5$ AIU/kg and from about 1 to about $1 \times 10^4$ SIU/kg of body weight per day. In some instances a sufficient therapeutic effect can be obtained at a lower dose, while in others, a larger dose will be required.

Oral administration is effected utilizing solid and liquid dosage unit forms such as powders, tablets, dragees, capsules granulates, suspensions, solutions and the like.

Powders are prepared by comminuting the compound to a suitable fine size and mixing with a similarly comminuted pharmaceutical carrier. Although an edible carbohydrate as for example starch, lactose, sucrose or glucose are conventionally used for this purpose, and can be utilized here as well, it is often desirable to employ a non-metabolizable carbohydrate such as a cellulose derivative. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the inhibitor when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated with a binder such as a syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Dosage unit formulations can also be microencapsulated. The formulation can moreover be prepared to prolong or sustain the release as for example by coating or embedding particulate material in polymers, wax of the like.

The toxicity of these compounds is very low. Even without final purification, the crude preparation of Example 8 having an activity of 26,000 SIU/g is tolerated without side effects. This is true of the compounds of the present invention described herein which have been tolerated at a dosage of 340,000 SIU/kg upon oral administration to mice and rats without adverse effects. On intravenous administration, mice tolerated 10,000 SIU/kg without side effects.

The pharmaceutical compositions according to the present invention can also contain other pharmaceutically active compounds, especially other orally-administrable antidiabetic agents. Examples of these are $\beta$-cytotropic sulphonylurea derivatives and bloodsugar-level-depressing biguanides.

In addition to the above pharmaceutical compositions, medicated foodstuffs can also be prepared. These comprise sugar, bread, potato products, fruit juice, beer, chocolate and other confectionery, and preserves such as jam, to which a therapeutically effective amount of at least one inhibitor of the present invention has been added.

The following examples will serve to further typify the nature of this invention. In these examples, representative ion exchange resins which can be used include AMBERLITE IRA 410 Cl- (anion exchanger); AMBERLITE IRC 120 (H+form) (strongly acid ion exchanger); AMBERLITE ($HCO_3$-form) (anion exchanger); AMBERLITE IRA 410 OH+(strongly basic ion exchanger); AMBERLITE IRC 50 H+ (weakly acid cation exchanger) and DOWEX 50 WX4 H+(strongly acid ion exchanger).

The microorganisms used herein have been deposited with the American Type Culture Collection under the following numbers:

| Strain | ATCC No. |
|---|---|
| SE 50 (CBS 961.70) | 310 42 |
| SE 18 (CBS 957.70) | 310 41 |
| SE 82 (CBS 615.71) | 310 45 |
| SE 50/13 (CBS 614.71) | 310 43 |
| SE 50/110 (CBS 674.73) | 310 44 |

EXAMPLE 1

A fermenter filled with 8 litres of nutrient solution containing 5.0% of starch, 1.0% of yeast extract and 0.2% of $K_2HPO_4$ is inoculated with a 3 day old shaken flask culture of the strain SE 50/13 (CBS 614.71) and the mixture is incubated with intensive stirring and aeration for 3 days at 28° C, giving a culture broth containing 105,000 AIU/ml.

6 litres of this culture broth are cooled to 20° C, the pH is adjusted to 2.5 with half-concentrated $HNO_3$, 30 g of Carboraffin active charcoal are added and the mixture is stirred for 10 minutes. It is then centrifuged at 10,000 rpm for 15 minutes and the clear light yellow supernatant liquid is neutralized with $NH_3$ and then concentrated to 500 ml. The 500 ml of concentrate were stirred for 45 minutes with 200 g of Amberlite IRA 410 Cl-, the latter was filtered off and the filtrate was treated with 4/5 of its volume (= 400 ml) of methanol in order to precipitate the bulk of the higher-molecular starch degradation products (together with active charcoal residues still present). The mixture is centrifuged for 5 minutes at 5,000 rpm. The 850 ml of supernatant liquid are added dropwise to 4 litres of dry spirit, with intensive stirring. The white flocculent precipitate is filtered off, washed 3 times with dry spirit and twice with ether and dried in vacuo at 50° C. Yield: 36 g of a white powder containing $10 \times 10^6$ AIU/g. This preparation is referred to below in several of the following Examples.

Enzyme Inhibition on Thin Layer Plates

To assess the end products of fermentation and the composition of the final preparation by means of thin layer chromatography, 1 $\mu$l of the fermentation broths or 1 $\mu$g of the preparations is applied to ready-to-use silica gel TLC films (Schleicher and Schüll, Dassel, type F 1,500) and the chromatogram is developed twice in n.-butanol/ethanol/water = 50/30/20(v/v).

To produce a saccharase inhibition coloration, the developed and well-dried plate is sprayed with enzyme gel (20 ml/20 × 20 cm plate) and the gel is allowed to solidify. The system is then pre-incubated for 5 minutes in a moist chamber at room temperature and then generously sprayed with substrate gel. After this 2nd gel layer has solidified, the plate is introduced into a moist chamber and incubated at 40° C. The inhibition coloration (light spots, red-brown background) develops in 60-90. At the point in time of optimum color development, the treatment is discontinued and the plate, with the agar layers thereon, is dried using a warm air blower.

Preparation of the gels

Enzyme gel: 1.5 g of agarose (from L'Industrie Biologique Francaise) is suspended in 100 ml of 0.2 M Na maleate buffer of pH 6.0 and then dissolved by boiling up. The clear agarose solution is cooled to 50° C and 250 μl of Triton X-100 solution (2 g of Triton X-100 + 8 g of analytical grade ethanol) and 0.5 ml of dianisidine solution (20 mg of dianisidine/1 ml of acetone) are added, with swirling. Directly before using the gel, 1 ml of GOD/POD reagent (12.5 mg of glucose oxidase, degree of purity I, Boehringer, order No. 15,423 and 2.5 mg of peroxidase, degree of purity II, Boehringer, order No. 15,302, dissolved in 5 ml of maleate buffer) and 4-5 saccharase units from the small intestine of the pig are added. The gel must be kept at 50° C until it is sprayed, since otherwise it solidifies in the nozzles during the spraying process.

Substrate gel: 0.5 g of agarose is suspended in 100 ml of Na maleate buffer of pH 6.0 and dissolved while boiling. The solution is then cooled to 50° C and 100 μl of Triton (2 g of Triton X-100 + 8 g of analytical grade ethanol) are then added, followed by 1 g of sucrose (Serva No. 35,579). After the sucrose has dissolved, the gel is ready to use.

For the amylase inhibition coloration, the developed and dried thin layer chromotography plate is sprayed with an amylase gel (20 ml/20 × 20 cm plate) and is allowed to solidify. After 5 minutes of pre-incubation at room temperature, the plate bearing the gel layer is introduced into an 0.5% strength starch solution (1 g of starch, Merck No. 1,252, dissolved, with boiling, in 200 ml of 0.2 M glycerophosphate buffer 0.01M $CaCl_2$, pH 6.9) and is left therein for 2 minutes at 40° C while swirling the solution. The plate is then well rinsed with distilled water and dipped into a dilute $I_2$ solution (4 ml of $I_2$ stock solution per 500 ml of $H_2O$; $I_2$ stock solution: 2.2 g of $I_2$ + 4.4 g of KI dissolved in 100 ml of $H_2O$) in orderto colour the starch which has not been degraded. After about 1 minute, the coloration is at optimum. It is photographed immediately since the blue spots fade rapidly.

Preparation of the amylase gel 1 g of agarose is dissolved in 100 ml of 0.2 M sodium glycerophosphate/0.01 M $CaCl_2$ buffer of pH 6.9 at 100° C and after cooling to 50° C, 100 μl of Triton X-100 (2 g of Triton X-100 + 8 g of analytical grade ethanol) are added. Directly before spraying, 100 μl of an amylase crystal suspension (10 mg of pig's pancreas amylase/ml of saturated $NH_4$ sulphate solution, Boehringer, No. 15,017) are added.

EXAMPLE 2

If a 1 litreErlenmeyer flask containing 120 ml of a nutrient solution consisting of 4% of starch, 2.4% of glucose, 0.9% of casein hydrolysate and 0.9% of yeast extract, pH adjusted to 7.6 with NaOH, mixed with 0.4% of $CaCO_3$ and sterilized for 30 minutes at 121° C, is inoculated with 3 ml of a pre-culture of the strain SE 82 (CBS 615.71), grown in a nutrient solution consisting of 2% of starch, 1% of glucose, 0.5% of casein hydrolysate and 1% of yeast extract, pH adjusted to 7.2 with NaOH, treated with 0.4% of $CaCO_3$ and sterilized for 30 minutes at 121° C, and the whole is incubated for 5 days at 28° C on a rotary shaking machine, a culture solution containing 122,000 AIU/ml is obtained. For working up, the mycelium is separated from the combined culture solution by centrifuging at 12,000 rpm, 300 ml of the culture filtrate are brought to pH 2.5 with half-concentrated $HNO_3$ and the mixture is stirred for 10 minutes with 2.5 g of analytical grade active charcoal. After separating off the charcoal at 12,000 rpm, the solution is neutralized to pH 6 with 10 N KOH, 300 ml of methanol are added, the mixture is allowed to stand briefly and the precipitate is removed at 12,000 rpm. If the supernatant liquid is now added dropwise to 3 liters of ethanol and the precipitate is isolated, after brief standing, by centrifuging at 12,000 rpm and is washed twice with absolute ethanol and once with ether and dried in vacuo, 2.23 g of a product containing 7.45 × $10^6$ AIU/g are obtained, which contains more than 95% of compounds having from 4 glucose units upwards.

EXAMPLE 3

If a 1l Erlenmeyer flask with 120 ml of a nutrient solution of composition 3.5% of glucose, 2% of starch 0.5% of casein hydrolysate, 1.3% of yeast extract, 0.3% of $CaCO_3$ and 0.3% of $K_2HPO_4$, adjusted to pH 7.8 before sterilization and sterilized for 30 minutes at 121° C, is inoculated with 6 ml of a pre-culture of the strain SE 50/110 (CBS 674.73) in a nutrient solution consisting of 3% of soya flour, 3% of glycerol and 0.2% of $CaCO_3$ and the mixture is incubated for 3-4 days on a rotary shaking machine at 24° C, a culture solution which contains 153,000 AIU/ml and 12,000 SIU/literis obtained.

1 liter of culture solution was adjusted to pH 2.5 with $HNO_3$ and the mixture was stirred for 10 minutes with 5 g of active charcoal and then centrifuged for 30 minutes at 5,000 rpm. It was then neutralized by adding 25 g of Amberlite IRA 410 (OH− form). The neutral supernatant liquid was concentrated to 100 ml on a rotary evaporator, mixed with 100 ml of methanol and filtered. The filtrate was stirred into 2 liters of dry spirit and the precipitate which separated out was filtered off, washed 3 times with acetone and ether and dried in vacuo.

Yield 14 g of a white powder containing 5 × $10^6$ AIU/g and predominantly containing compounds having from 4 glucose units upwards.

EXAMPLE 4

If the procedure of Example 3 is followed but with the addition of 0.5% starch, a culture broth containing 40,000 AIU and 184 SIU/ml is obtained after 4 days' fermentation. The culture broth contains a mixture of compounds of the invention having from one glucose unit upwards.

EXAMPLE 5

If a 1 liter Erlenmeyer flask which contains 120 ml of nutrient solution of composition 3% of glucose, 0.6% of casein hydrolysate, 1.6% of yeast extract, 0.3% of $CaCO_3$ and 0.3% of $K_2HPO_4$, pH adjusted to 7.8 with KOH before sterilization, is inoculated with a pre-culture of the strain Se 50/110 (CBS 674.73) according to Example 3 and incubated for 4 days at 24° C on a rotary shaking machine, a culture broth of 10,800 SIU/liter, which predominantly contains the compound of the invention having one glucose unit, is obtained.

5 liters of culture filtrate, separated from the mycelium at 13,000 rpm, were adjusted to pH 2.5 with half-concentrated $HNO_3$ and stirred for 15 minutes with 55 g of active charcoal ("Merck") and 200 g of Clarcel. After removing the solids by suction filtration, the filtrate was neutralized to pH 7 with concentrated ammonia and the solution was concentrated to 1.5 liter and precipitated with a five-fold amount of ethanol. The resulting flocculent precipitate was separated off using a continuous flow rotor at 12,000 rpm and the yellowish supernatant liquid was concentrated to 150 ml and centrifuged at low speed to separate off minor proportions of undissolved material. 50 ml of this solution were charged onto a column filled with Amberlite IR-120 ($H+$ form) (30 × 300 mm; 30 ml of $H_2O$ per hour). After a total of 300 ml of eluate, which contains inert saccharides and a proportion of nonadsorbed components having an inhibiting action, had been collected, the exchanger was transferred into a beaker with about 400 ml of $H_2O$ and concentrated ammonia was added, while stirring, until the pH had reached a value of 11.5. After stirring for a further 30 minutes, the exchanger was separated off, the liquid was concentrated to 1/20 of its volume and filtered through a column (20 × 150 mm) containing Amberlite IRA-410 ($HCO_3^-$ form) and about 500 ml of eluate were collected at a flow speed of 30 ml/hour; the eluate was concentrated and after lyophilization gave 1.3 g of crude product.

For further purification, the crude product was fractionated on Bio-Gel P-2, 100-200 mesh ( Bio-Rad, Munich). A column of 50 mm diameter and 450 mm length was used for this purpose and was operated with $H_2O$ at a flow speed of 40 ml per hour, fractions of 10 ml each being collected. All fractions were tested by means of the anthrone test for carbohydrates and by means of the saccharase inhibition test for components having an inhibiting action. The fractions containing saccharase inhibitor were further examined by thin layer chromatography, in accordance with Example 1, for their content of individual components. The fractions which contained the compound having one glucose unit were combined, concentrated and lyophilized. 35 mg of material showing $0.3 \times 10^6$ AIU/g and 30,000 SIU/g, were obtained.

EXAMPLE 6

If 1 l Erlenmeyer flasks each containing 120 ml of a nutrient solution of composition 5% of starch, 1% of yeast extract and 0.2% of $K_2HPO_4$ are each inoculated with 2 ml of a pre-culture according to Example 3 and incubated for 3 days at 28° C, culture solutions with the following yield of amylase inhibitor are obtained:

| Strain | AIU/ml |
| --- | --- |
| SE 50 (CBS 961,70) | 37,000 |
| SE 50/13 (CBS 614.71) | 109,000 |
| SE 50/110 (CBS 674.73) | 53,500 |

The mixture consists predominantly of a mixture of compounds with four or more glucose units.

EXAMPLE 7

If 1 l Erlenmeyer flasks each containing 120 ml of nutrient solution of composition 1.3% of maltose, 3.5% of glucose, 0.5% of casein hydrolysate, 1.3% of yeast extract, 0.3% of $CaCO_3$ and 0.3% of $K_2HPO_4$ are each inoculated with 2 ml of a pre-culture according to Example 3, the following yields are obtained after 4 days' incubation with various strains on rotary shaking machines at 24° C:

| Strain | SIU/ml | AIU/ml |
| --- | --- | --- |
| SE 50 (CBS 961.70) | 25 | 580 |
| SE 50/13 (CBS 614.71) | 14.8 | 1,460 |
| SE 50/110 (CBS 674.73) | 57.9 | 755 |

The products consist predominantly of a mixture of compounds having four or less glucose units.

EXAMPLE 8

If a fermenter containing 100 l of nutrient solution of composition 3.5% of glucose, 2.5% of dry powdered malt extract, 0.5% of casein hydrolysate, 1.3% of yeast extract, 0.3% of $CaCO_3$, 0.3% of $K_2HPO_4$ and 0.1% of anti-foaming agent is inoculated with 5 l of a pre-culture according to Example 3 and incubated for 5 days at 24° C with stirring and aeration, a culture solution of 73,000 SIU/l is obtained, which predominantly contains the compound of the invention with n = 2.

A 90 liter fermentation batch together with the mycelium is adjusted to pH 2.5 on a pH meter by means of concentrated $HNO_3$ and 900 g (=1%) of active charcoal (Merck) are added while stirring in order to adsorb the bulk of the dyestuffs formed. The mixture is stirred for 15 minutes, the mycelium and the bulk of the charcoal were separated off on a centrifuge at 3,000 rpm and the supernatant liquid, with addition of 3 kg of Clarcel, is finally filtered through a pressure filter. 65 l of yellow-brown, clear filtrate of SIU content 60,000 SIU/litre are obtained.

The filtrate is adjusted to pH 7 with concentrated $NH_3$ and stirred with 1,300 g (2%) of active charcoal (Merck) for 30 minutes in order to adsorb the active substance. The mixture is filtered through a pressure filter and the active charcoal sediment was washed 3 times with 10 liters of distilled water. The charcoal is then thoroughly pressed dry and stirred with 3 times 4 liters of 50% strength acetone at pH 2.5, in each case for 15 minutes, so as to desorb the active substance from the charcoal. The acetone desorbates are combined after removing the charcoal by filtration. The combined desorbate is concentrated to 250 ml on a rotary evaporator, an equal volume (250 ml) of methanol is added and the mixture is filtered through a folded filter. The filtrate (480 ml) is added dropwise to 5 litres of acetone, with vigorous stirring. The precipitate which separated out is filtered off and washed 3 times with acetone and ether. It is then dried in vacuo at 35° C. Yield 230 g of crude product containing 8,500 SIU/g.

25 g of the above crude product are dissolved in 1 liter of $H_2O$ and stirred with 300 g of Dowex 50 WX 4 $H+$(200–400 mesh) for 30 minutes. The resin is filtered off and rinsed 3 times with 2 liters of 0.001 N HCl. The washed Dowex is then suspended in 500 ml of $H_2O$ and the suspension adjusted to pH 9.0 on a pH meter by addition of 25% strength $NH_3$ Thereafter 2 further desorptions are carried out, each with 500 ml of 0.6% strength of $NH_3$ and the desorbates are combined and concentrated to 100 ml on a rotary evaporator. To decolorize this concentrate, it is stirred for 5 minutes with 2 g of DEAE-cellulose (Schleicher and Schüll, No. 02035, 0.6 milliequivalent/g), and then centrifuged. The light yellow supernatant liquid is mixed with an equal volume (100 ml) of methanol and the mixture is then added dropwise to 2 liters of acetone, with intensive stirring. The precipitate is filtered off, washed with acetone and ether and dried in vacuo at 35° C.

For additional fine purification, the 4.0 g of inhibitor are gel-filtered, in 0.5 g portions, through Biogel P-2. For this purpose, each 0.5 g of the preparation is dissolved in 10 ml of $H_2O$ and the solution was charged onto a Biogel P-2 column (200-400 mesh, Bio-Rad) of 5 cm diameter and 95 cm length. The column is developed in water at a flow rate of 80 ml/hour. 12 ml fractions are collected. For all fractions, the total carbohydrate content (in the form of the anthrone test, as an extinction at $E_{620}$) and the content of saccharase inhibitor and amylase inhibitor is determined. In addition, the fractions are tested by thin layer chromatography (enzyme inhibition coloration according to Example 1).

The fractions containing the compounds with 4-6 glucose units are combined, concentrated to 10 ml in vacuo and precipitated by dropwise addition to 200 ml of dry spirit. The precipitate is centrifuged off, washed with acetone and ether and dried in vacuo; yield from 4.0 g of crude inhibitor: 0.2 g of compounds having 4 to 6 glucose units with activity of $17.5 \times 10^6$ AIU/g and 8,500 SIU/g. The fractions containing the compound with 3 units are worked up in the same manner, the precipitation being carried out with 200 ml of acetone; yield from 4.0 g of crude inhibitor: 0.1 g of compound of the invention with 3 units, containing $1.4 \times 10^6$ AIU/g and 21,000 SIU/g. 0.9 g of the compound of the invention with 2 units containing $0.3 \times 10^6$ AIU/g and 68,000 SIU/g is isolated from the fractions (precipitation with acetone) containing the compound having 2 glucose units.

EXAMPLE 9

If 3 small fermenters each containing 8 liters of a nutrient solution with 7.5% of dry powdered malt extract, 0.3% of casein hydrolysate, 0.7% of yeast extract, 0.3% of $CaCO_3$ and 0.3% of $K_2HPO_4$ are inoculated with 5% of a preculture of the strain SE 50/110 (CBS 674.73) (obtained according to Example 3), 5 days' incubation at 24° C gives a culture broth of 73 SIU/ml which predominantly contains compound with two glucose units. After centrifuging (30mins., 3,000 rpm) to separate off the mycelium, 20.5 liters of a deep brown culture solution containing 67,000 SIU/l were obtained. This solution is adjusted to pH 3.5 with $HNO_3$ and 60 g of Lewapol (Ca 9221, 0.35 mm particle size, Bayer A. G.) /l = 1.23 kg of Lewapol were added to decolourize the solution. After stirring for 20 minutes, the mixture is filtered using a Seitz K 3 filter. The decolorized culture solution is neutralized with $NH_3$ (18.5 l, 67,000 SIU/l). 20 g of active charcoal/l = 370 g are then stirred in to adsorb the active substance, and the mixture was stirred for 30 minutes. It is then filtered through a K 3 filter which is covered with a layerof the filter aid Clarcel. The filtrate (17.5 l, 3,600 SIU/l) is discarded. The charcoal residue is washed 3 times with 2 l of distilled $H_2O$. To desorb the active substance from the charcoal, the latter is stirred 3 times in succession, each time for 15 minutes, with 1 l of 80% strength acetone at a time, the pH being adjusted to 2.5 with concentrated HCl. The desorbates are combined (2.4 l, 371,000 SIU/l). 20 g of Dowex H+/l (Dowex 50W × 4, H+form, Serva, Heidelberg) = 46 g of Dowex were introduced into this desorbate and the mixture was stirred for 20 minutes. The resin is then filtered off (Dowex fraction I) and rinsed with a little 75% strength acetone. The filtrate and wash liquid (3 l = 215,000 SIU/l) are stirred with 60 g of Amberlite IRA 410 (OH−form) (Messrs. Serva, Heidelberg)/l until pH 7 was reached. The mixture is then filtered and the filtrate (2.8 l, 219,000 SIU/l) is mixed with 72 g of Dowex H+and stirred for 20 mintes. While doing so, the pH is kept at 3.0 by hanging a porous nylon pouch, filled with Amberlite 410 OH−, into the mixture. The Dowex is then filtered off (Dowex fraction II) and the filtrate (2.6 l, 27,000 SIU/l) is discarded.

The Dowex fractions I and II are each washed individually 3 times with 75% strength acetone at pH 3.5 and then each desorbed 3 times with 100 ml of 0.6% strength $NH_3$ at a time (Dowex fraction I) or with 150 ml of 0.6% strength $NH_3$ at a time (Dowex fraction II). During the first desorption, during which the amount of ammonia does not suffice to neutralise the Dowex resin, the pH is adjusted to 9 on a pH meter by addition of concentrated $NH_3$. The three desorbates from Dowex fraction I and II are respectively combined, concentrated almost to dryness on a rotary evaporator, taken up in 50 ml of $H_2O$, adjusted to pH 3-4 on a pH meter by means of HCl, and mixed with 50 ml of methanol. The solutions are added dropwise to 1.5 l of absolute acetone, while stirring, and the precipitate formed is filtered off and washed 3 times with acetone and once with ether. It is dried in vacuo.

Yield:
Fraction I 6.5 g 25,000 SIU/g
Fraction II 12.3 g 36,000 SIU/g

Fraction I and II mainly contain, as the inhibiting constituents, the compound of the invention with 2 glucose units in addition to small proportons of the compound having 3 glucose units.

The following Table shows the saccharase-inhibiting activities of the preparation at successive stages.

| Yield | Volume (l) | SIU/l | Total SIU | | % | Yield of SIU | |
|---|---|---|---|---|---|---|---|
| 1) Culture solution | 20.5 | 67,000 | 1,373,500 | | | 100 | |
| 2) After discolouration with Lewapol | 19.5 | 67,000 | 1,306,500 | | | 95 | |
| 3) After active charcoal adsorption | 18.5 | 3,600 | 66,600 | | | (4.8 discarded) | |
| 4) 1st desorbate | 0.7 | 742,000 | 519,400 | } | | 37.8 | |
| 5) 2nd desorbate | 0.9 | 329,000 | 296,100 | } 883,500 | | 21.6 } | 64.4 |
| 6) 3rd desorbate | 0.8 | 85,000 | 68,000 | } | | 5.0 } | |
| 7) Mixed desorbate (4-6) | 2.4 | 371,000 | 890,400 | | | 64.8 | |
| 8) After 1st Dowex adsorption | 3.0 | 215,000 | 645,000 | | | | |
| 9) After neutralisation with IRA OH− | 2.8 | 219,000 | 613,200 | | | | |
| 10) After 2nd Dowex adsorption | 2.5 | 27,000 | | 67,500 | | (4.9 discarded) | |
| 11) Combined $NH_3$ desorbates of Dowex fraction I | 0.29 | 682,000 | | 197,780 | | 14.4 } | 60,9 |

| Yield | Volume (1) | SIU/1 | Total SIU % | Yield of SIU | |
| --- | --- | --- | --- | --- | --- |
| 12) Combined NH₃ of Dowex fraction II | 0.45 | 1,419,000 | | 638,550 | 46.5 |
| 13) Precipitate, Fraction I | 6.5 g | 25,000 /g | | 162,500 | 11.8 ⎫ |
| Precipitate, Fraction II | 12.3 g | 36,000 /g | | 442,800 | 32.2 ⎬ 44,0 |

EXAMPLE 10

200 g of a preparation as described in Example 1 were dissolved in 940 ml of distilled water and 60 ml of concentrated $H_2SO_4$ and the mixture was warmed under reflux for 4 hours (internal temperature: 98° –100° C; oil bath temperature: 140° C). 10 g of active charcoal (Merck Art. 2186) were added to the cooled black-brown solution and the mixture was stirred for 1 hour. The active charcoal was then filtered off and washed with water and the filtrate was adjusted to pH = 7 to 8 with about 250 ml of 10 N KOH. The solution was stirred for 1 hour with 50 g of active charcoal. The charcoal was filtered off and washed with 2 l of water and the filtrate was discarded. For desorption, the charcoal was digested overnight with 2 l of 30% strength alcohol. Finally, the charcoal was filtered off and the alcoholic solution was concentrated on a rotary evaporator. Residue: 6.2 g. This crude product (6.2 g) was dissolved in 500 ml of water and the solution was gently stirred with 30 g of Amberlite IR 120 (H+form) for 1 hour. The exchanger was filtered off and washed with distilled water until the filtrate was neutral and free from glucose. The exchanger was then stirred overnight with 15 ml of 25% strength $NH_3$ in 1,000 ml of $H_2O$, separated off and discarded. The filtrate was concentrated on a rotary evaporator.

Residue: 3.7 g.

For further purification, a chromatography on cellulose was carried out. 4.5 g of the material desorbed from the exchanger were applied to a 1 m long and 2.5 cm wide column filled with cellulose. The running agent used was initially 5:1 ethanol/$H_2O$, and 3:1 ethanol/$H_2O$ was initially used to eluate the compound of the invention with n = 1. Fractions of 14 ml were collected at a drip speed of 20 drops per minute. The individual fractions were examined by thin layer chromatography. Fractions 47–85 gave, after concentration, 1.6 g of a compound of the invention with one glucose unit exhibiting a pale brownish discoloration. The discoloring impurities were quantitatively insignificant. The compound with one glucose unit was obtained as a colorless resin if the purification step with a strongly acid ion exchanger was carriedout on a column and not by the batch process.

EXAMPLE 11

200 g of a preparation as described in Example 1 were dissolved in 940 ml of distilled water and 60 ml of concentrated $H_2SO_4$ and the solution was warmed under reflux for ¼ hour (internal temperature: 98° –100° C; oil bath temperature: 140° C). 10 g of active charcoal (Merck, Art. 2186) were added to the cooled black-brown solution and the mixture was stirred for 1 hour. The active charcoal was then filtered off and washed with water and the filtrate was adjusted to pH = 7 to 8 with about 250 ml of 10 N KOH. The solution was stirred with 50 g of active charcoal for 1 hour. The charcoal was filtered off and washed with 2 l of water and the filtrate was discarded. For desorption, the charcoal was digested overnight with 2 l of 30% strength alcohol. Finally, the charcoal was filtered off and the alcoholic solution was concentrated on a rotary evaporator.

Residue: 8.0 g.

The residue was taken up in 15 ml of $H_2O$ and applied to a column (height: 20 cm, diameter 2.4 cm) filled with 50 g of Amberlite IR 120 (H+form). The solution was absorbed at 3 drops/minute and the column was rinsed with water (12 drops/minute) until all non-basic constituents had been removed. The basic products were then eluted from the column with 0.5% strength $NH_3$ (12 drops/minute) and the aqueous solution was evaporated to dryness on a rotary evaporator.

Residue: 4.1 g.

2 g of this residue were dissolved in a little water and applied to a column (height: 200 cm; $\phi$: 3.0 cm) filled with Sephadex G-15. The column was eluted with water. Fractions of 2 ml each were collected at a flow speed of 8 ml/hour. The individual fractions were examined by thin layer chromatography. Fractions 85–94 gave 280 mg of the compound having 2 glucose units and a specific activity of 50,000 SIU/g.

EXAMPLE 12

If 2 g of a preparation as described in Example 1, in 60 ml of 20 mM sodium glycerophosphate buffer of pH 6.9, containing 1 mM of $CaCl_2$, are incubated with 1 g of α-amylase from Aspergillus spec. (SERVA No. 13,418) for 120 hours at 37° C with constant stirring and finally heated to 100° C for 5 minutes, and undissolved matter is centrifuged off at 4,000 rpm, lyophilization of the solution gives 1.9 g of a product with 3,500 SIU/g and 2 × 10⁶AIU/g. If this product is tested by thin layer chromatography and saccharase inhibition discoloration as described in Example 1, it is found that the compounds having an inhibiting action which are present are essentially the compounds of the invention with 1, 2 and 3 glucose units.

EXAMPLE 13

If 2 g of a preparation as described in Example 1, in 30 ml of 20 mM acetate buffer of pH 4.8, are incubated with 1.25 mg of β-amylase from sweet potato (BOEHRINGER 15,471) for 120 hours at 37° C, with constant stirring and finally heated to 100° C for 5 minutes, and undissolved matter is centrifuged off at 4,000 rpm, lyophilization of the solution gives 1.5 g of a product with 1,800 SIU/g and 3.8 × 10⁶ AIU/g. If this product is tested by thin layer chromatography and saccharase inhibition discoloration as described in Example 1, it is found that the compounds having an inhibiting action which are present are essentially the compounds of the invention with 2 and 3 glucose units.

EXAMPLE 14

If a 200 ml Erlenmeyer flask containing 25 ml of a nutrient solution of composition 0.1% $K_2HOP_4$, 0.2% of $(NH_4)_2SO_4$, 0.05% of $MgSO_4$, 0.05% of KCl, 0.01% of $FeSO_4$ and 2% of a preparation as described in Example 1 is inoculated with a spore suspension of the strain Asp. niger ATCC 11,394 and incubated at 28° C on a rotary shaking machine, the AIU concentration falls from 210,000 AIU/ml to 53,000 AIU/ml after 6 days and to 21,300 AIU/ml after 10 days. At the same time the SIU/ml content rises from 7.0 to 72 SIU/ml.

20 ml of a solution which has been incubated with the spore suspension for 10 days are centrifuged for 30 minutes at 3,000 rpm to separate off the mycelium. 15 ml of supernatant liquid (72,000 SIU/l) are desalinated by stirring for 30 minutes with 2 g of Amberlite IRC 50 H+ and 1 g of Amberlite IRA 410 OH− (conductivity less than 2 mS·cm⁻¹). The mixture is filtered and the filtrate allowed to run at the rate of 5 ml/hour through a column (1 cm × 10 cm) of Dowex H+ equilibrated in 0.001 N HCl. The column is then rinsed with 200 ml of 0.001 N HCl. For desorption, 0.6% strength NH₃ solution is pumped through the column (10 ml/hour) and 5 ml fractions are collected. The fractions containing the saccharase-inhibiting activity are combined, concentrated to 2 ml on a rotary evaporator and mixed with 2 ml of methanol. This solution is adjusted to pH 3–4 and precipitated by adding it dropwise to 100 ml of acetone. The precipitate is filtered off, washed with acetone and ether and dried in vacuo. Yield: 26 mg containing 28,000 SIU/g and consisting of compounds with 2 and 3 glucose units. The isolation of the pure compound with 2 glucose units from this product is effected as described in Example 8 by gel filtration through a column containing Bio-Gel P-2. 7 mg of the compound with 2 glucose units of 60,000 SIU/g, are obtained.

EXAMPLE 15

2 liters of culture filtrate obtained from a fermentation batch as described in Example 5 by centrifuging off the mycelium at 13,000 rpm and having an activity of 13,000 SIU/g were stirred with 500 g of a mixture of 2.5 parts of Amberlite IRC-50 (H+ form) and 1 part of Amberlite IRA-410 (OH' form) for 1 hour in order to reduce the salt content (conductivity of the culture filtrate: about 10 mS ·cm⁻¹). The exchanger was separated off and the solution was concentrated to a little less than 100 ml and centrifuged for 15 minutes at 20,000 rpm to remove undissolved constituents. The supernatant liquid was made up to 100 ml; it now had a conductivity of 3.5 mS ·cm⁻¹) and was further purified by applying it to a column (55 × 400 mm) of P-cellulose (SERVA No. 45,130, pre-treated according to known methods and equilibrated in 5 mM ammonium phosphate buffer, pH 5.5). The abovementioned phosphate buffer served as the running agent; the flow rate was 90 ml/hour and fractions of 18 ml volume were collected.

After the fractions of the eluate had been tested for their carbohydrate content (by means of the anthrone test) and for their content of saccharase-inhibiting components (by means of the saccharase inhibition test), the fractions which in the anthrone test had proved almost free of carbohydrates and equally in the saccharase inhibition test had proved particularly active were combined (fractions 60–170), concentrated to 150 ml and filtered through a column (50 × 300 mm) containing Amberlite IRA-410 (HCO₃⁻-form). For better control of the deionisation, the eluate was collected in fractions (10 ml per fraction in 20 minutes) and tested for carbohydrate (by means of the anthrone test: in each case virtually negative), for phosphate (by means of ascorbic acid-molybdate reagent: in each case negative) and for saccharase inhibition (by means of the enzyme inhibition test). The fractions having an inhibiting action (3–30) were combined, concentrated, lyophilized, redissolved and lyophilized so as to give 280 mg of crude inhibitor.

For further purification, the crude inhibitor was fractionated on Bio-Gel P-2 as described in Example 5. From the fractions which contained, pure, the compound with one glucose unit, 30 mg of a product with $0.3 \times 10^6$ AIU/g and 35,000 SIU/g were isolated after lyophilization.

EXAMPLE 16

To isolate the compounds with 5–7 glucose units the starting material used can be, for example, a preparation such as described in Example 1.

For this purpose, 30 g of the preparation according to Example 1 were dissolved in 250 ml of H₂O. The conductivity of the resulting solution was 10 mS·cm⁻¹ and the pH was 5,5. The solution was desalinated by adding 60 g of Amberlite IRC 50 H+ (weakly acid cation exchanger which only binds traces of the amino-sugar derivatives from aqueous solution) and 20 g of Amberlit IRA 410 OH− and stirring for 20 minutes. The filtrate (conductivity 0.5 mS·cm⁻¹, pH 3.5) was adjusted to pH 3.0 with 1 N HCl (conductivity 0.6 mS·cm⁻¹). This solution was pumped at the rate of 42 ml/hour through a column filled with Dowex 50 W × 4, 200–400 mesh. (H·) (⌀2.5 cm, height 40 cm, equilibrated in 0.001 N HCl) and the Dowex was then rinsed with 2 l of 0.001 N HCl. After washing the column, elution was carried out with 1.2% strength aqueous ammonia and 10 ml fractions were collected. The fractions having an inhibiting action were combined, the ammonia was stripped off in vacuo and the solution was then concentrated in vacuo to 30 ml. The product was precipitated by dropwise addition to 600 ml of dry spirit and the precipitate was filtered off, washed with alcohol and ether and dried in vacuo. Yield 4.4 g, containing $26.5 \times 10^6$ AIU/g.

0.5 g portions were subjected to a fine purification by application to a preparative Biogel P-2 column, as described in Example 8, and development. The fractions which according to a thin layer chromatogram (amylase inhibition coloration) contain compounds with 5 to 7 glucose units were combined, concentrated in vacuo and precipitated with dry spirit as described above. Yield from 0.5 g of crude product: 0.2 g of amino-sugar derivatives with 5 to 7 glucose units containing $30 \times 10^6$ AIU/g and 2,500 SIU/g.

EXAMPLE 17

This example illustrates how the compounds of the invention can be eluted from cation exchanger under acid conditions.

A column of 1.5 cm. diameter is filled with 30g. (wet weight) of Dowex 50 W × 4, (H+) 200–400 mesh in 0.001 n HCl. Finally 500 ml. of mixed desorbate (400 000 SIU/L), pH 2.5, 60% acetone), obtained according to Example 9 (Table, run No. 7) are pumped through the column in about 1 hour and washed finally with 500 ml of 0.001 N HCl. Under these conditions only trace activity is eluted. Finally desorption therefrom with 0.125 N HCl was effected, the column eluate being monitored by conductivity or refractometry. The SIU content of the eluate was also tested. The active fractions 74–100 were combined and neutralized by the addition of Amberlite IRA 410 OH³¹, then reduced to 5 ml, reacted with 5 ml of methanol, and precipitated by dropping into 200 ml acetone. After washing with acetone and ether vacuum-drying was effected.

Yield 1 g of the compound with two glucose units with 65,000 SIU/g.

From the active initial fraction the compounds with 3 and 4 glucose units could be obtained.

This process of acid desorption therefore makes possible in contrast to the alkaline desorption, fractionation of the individual amino sugar derivatives of this series. Subjecting material prepared as above having 4 to 8 glucose units to this process but simply lyophilizing the neutralized eluates, the individual higher fractions are obtained as follows:

4 glucose units = 67,000 AIU/mg
5 glucose units = 57,000 AIU/mg
6 glucose units 32 42,000 AIU/mg
7 glucose units 32 24,000 AIU/mg
8 glucose units 32 5,000 AIU/mg

EXAMPLE 18

The β-amylase degradation procedure described above is performed as follows.

100 mg of compound were dissolved in 1.9 ml of 20 mM sodium acetate buffer (pH 4.75) and 0.1 ml of sweet potato β-amylase (BOEHRINGER No. 15471; 5 mg/ml; 500 U/mg) were added. The mixture was incubated at 37° C for 48 hours, heated to 100° C for 5 minutes and then centrifuged at 4500 rpm to remove precipitated protein and other impurities. The entire mixture was then applied to a column (22 mm diameter; 1,000 mm in length; thermostatedly controlled at 65° C) and eluted with water at a flow rate of 25 ml/hour. The eluate is monitored by a conductometer and a high-sensitivity refractometer equipped with flow-through cells. Fractions of 2.5 ml each were collected. The fractions can be tested for amylase or saccharase inhibiting activity or for carbohydrate content by means of the anthrone reaction. Electrolytes originating from the buffer and the enzyme preparation are eluted with the void volume and the degradation products are eluted according to decreasing molecular weight. Complete separation of compounds with small differences in molecular weight is effected by recycling chromatography using the same conditions as described above. Fractions containing products which are to be isolated are pooled and lyophilized.

EXAMPLE 19

For the separation of the isomeric compounds having three glucose units, 10 g of a mixture of isomers dissolved in water were applied to a column (25 by 500 mm) filled with Dowex - 50 W X 4 (H+). The column was first washed with water until the eluate was neutral and then eluated with 0.025 N hydrochloric acid. Fractions of 3 ml each were collected and tested by thinlayer chromatography. Thinlayer chromatography was performed on silanized silica gel plates (Merck, Germany) with 100 : 60: 40 : 2 ethylacetate + methanol + water + 25 % ammonia with threefold development. The compound with formula IV travels a wider distance from the origin than does the compound with formula V. Fractions 215 through 272 containing 6 g isomer with formula V and fractions 288 through 294 containing 600 mg isomer with formula IV were pooled, neutralised with Amberlite IRA - 410 (OH−) and evaporated.

The in vitro saccharase inhibiting activity of the isomer with formula IV isolated by this procedure is 19.000 SIE/g.

What is claimed is:

1. The compound 0-{4,6-bisdesoxy-4-[1S-(1,4,6/5)-4,5,6-trihydroxy-3-hydroxymethylcyclohex-2-en-1-ylamino]-α-D-glucopyranosyl}-(1→4)-D-glucopyranose of the conformational structural formula:

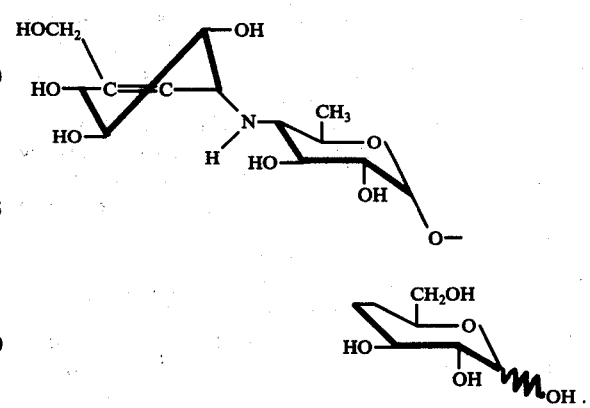

2. The method of inhibiting glucoside hydrolases in the digestive tract of humans and animals which comprises administering thereto at least an effective inhibitory amount of a compound according to claim 1.

3. A pharmaceutical composition for effecting inhibition of glucoside hydrolases in humans and animals comprising an effective inhibitory amount of a compound according to claim 1 in combination with an inert, compatible pharmaceutical carrier.

4. A foodstuff composition for effecting inhibition of glucoside hydrolases in humans and animals comprising an effective inhibitory amount of a compound according to claim 1 in combination with an inert, compatible foodstuff carrier.

5. The compound 0-{4,6-bisdesoxy-4[1S-(1,4,6/5)-4,5,6-trihydroxy-3-hydroxymethycyclohex-2-en-1-ylamino]-α-D-glucopyranosyl}-(1→4)-0-α-D-glucopyranosyl-(1→4)-D-glucopyranose of the conformational structural formula:

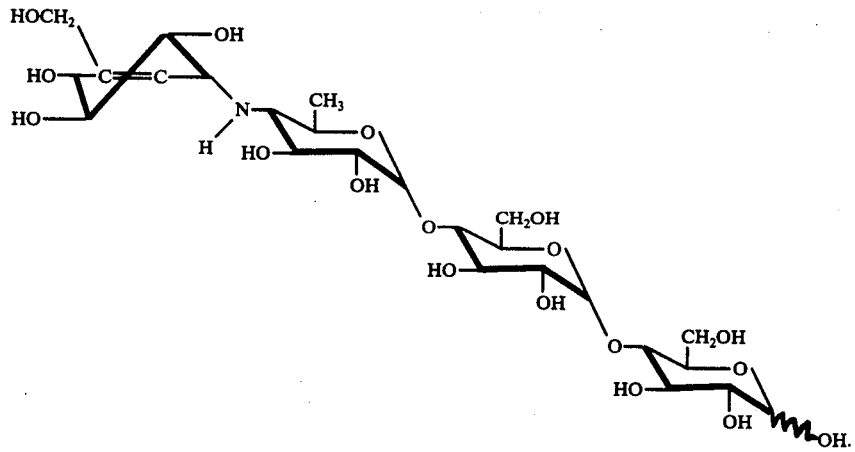

6. The method of inhibiting glucoside hydrolases in the digestive tract of humans and animals which comprises administering thereto at least an effective inhibitory amount of a compound according to claim 5.

7. A pharmaceutical composition for effecting inhibition of glucoside hydrolases in humans and animals comprising an effective inhibitory amount of a compound according to claim 5 in combination with an inert, compatible pharmaceutical carrier.

8. A foodstuff composition for effecting inhibition of glucoside hydrolases in humans and animals comprising an effective inhibitory amount of a compound according to claim 5 in combination with an inert, compatible foodstuff carrier.

9. The compound 0-{4,6-bisdesoxy-4-[1 S-(1,4 6/5)-4,5,6-trihydroxy-3-hydroxymethylcyclohex-2-en-1-ylamino]-α-D-glucopyranosyl}-(1→4)-0-α-D-glucopyranosyl-(1→4)-0-α-D-glucopyranosyl-(1→4)-D-glycopyranose of the conformational structural formula:

10. The method of inhibiting glucoside hydrolases in the digestive tract of humans and animals which comprises adminstering thereto at least an effective inhibitory amount of a compound according to claim 9.

11. A pharmaceutical composition for effecting inhibition of glucoside hydrolases in humans and animals comprising an effective inhibitory amount of a compound according to claim 9 in combination with an inert, compatible pharmaceutical or carrier.

12. A foodstuff composition for effecting inhibition of glucoside hydrolases in humans and animals comprising an effective inhibitory amount of a compound according to claim 9 in combination with an inert, compatible foodstuff carrier.

13. The compound 0{4,6-bisdesoxy-4-[1 S-(1,4,6/5)-4,5,6-trihydroxy-3-hydroxymethyl-4-0-α-D-glycopyranosyl-(1→4)-cyclohex-2-en-1-ylamino]-α-D-glycopyranosyl}-(1→4)-0-α-D-glucopyranosyl-(1→4)-D-glucopyranose of the conformational structural formula:

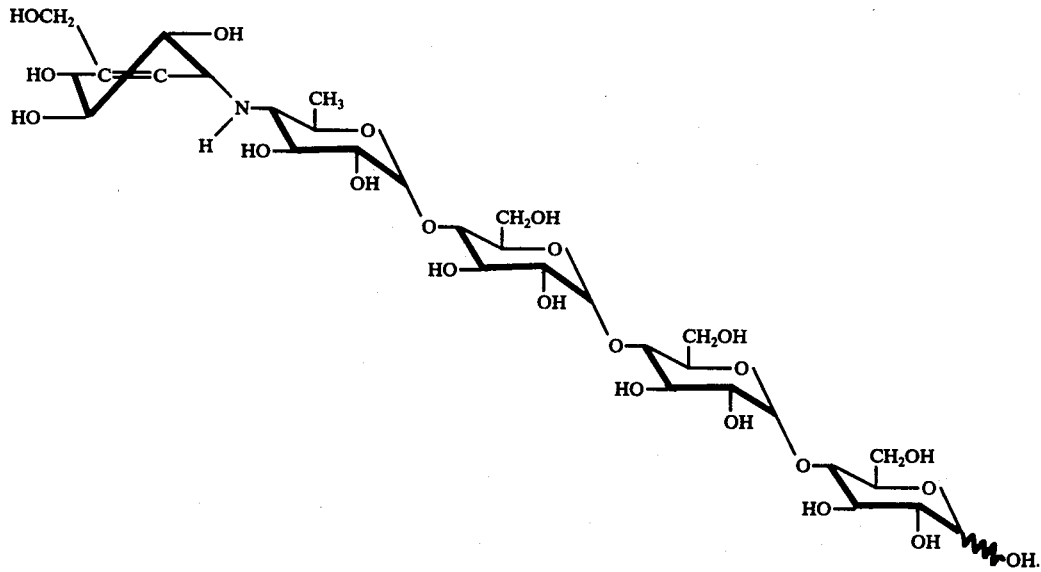

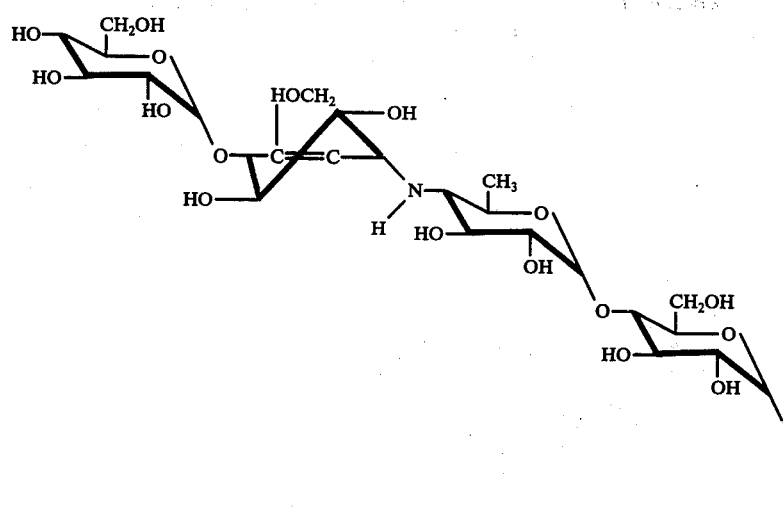

14. The method of inhibiting glucoside hydrolases in the digestive tract of humans and animals which comprises administering thereto at least an effective inhibitory amount of a compound according to claim 13.

15. A pharmaceutical composition for effecting inhibition of glucoside hydrolases in humans and animals comprising an effective inhibitory amount of a compound according to claim 13 in combination with an inert, compatible pharmaceutical carrier.

16. A foodstuff composition for effecting inhibition of glucoside hydrolases in humans and animals comprising an effective inhibitory amount of a compound according to claim 13 in combination with an inert, compatible foodstuff carrier.

17. An amino sugar produced by microorganisms of the family Actinoplanaceae consisting of a 4,6-bisdesoxy-4-(4,5,6-trihydroxy-3-hydroxymethylcyclohex-2-en-1-ylamino)-α-D-glucopyranose of the formula:

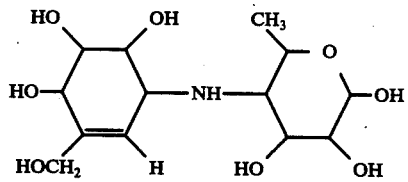

glycosidically linked with $n$ glucose units, where $n$ is 4, 5, 6, 7 or 8, which units are present as either one or two α-1:4 oligosaccharide chains or as one glucose unit and one α-1:4 oligosaccharide chain, said amino sugar yielding upon total acid hydrolysis the compound

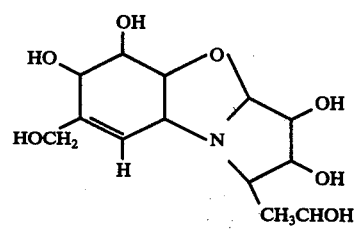

and glucose in a molar ratio of 1:$n$ wherein $n$ is as defined above.

18. An amino sugar according to claim 17 wherein $n$ is 4.

19. An amino sugar according to claim 18 which has the formula:

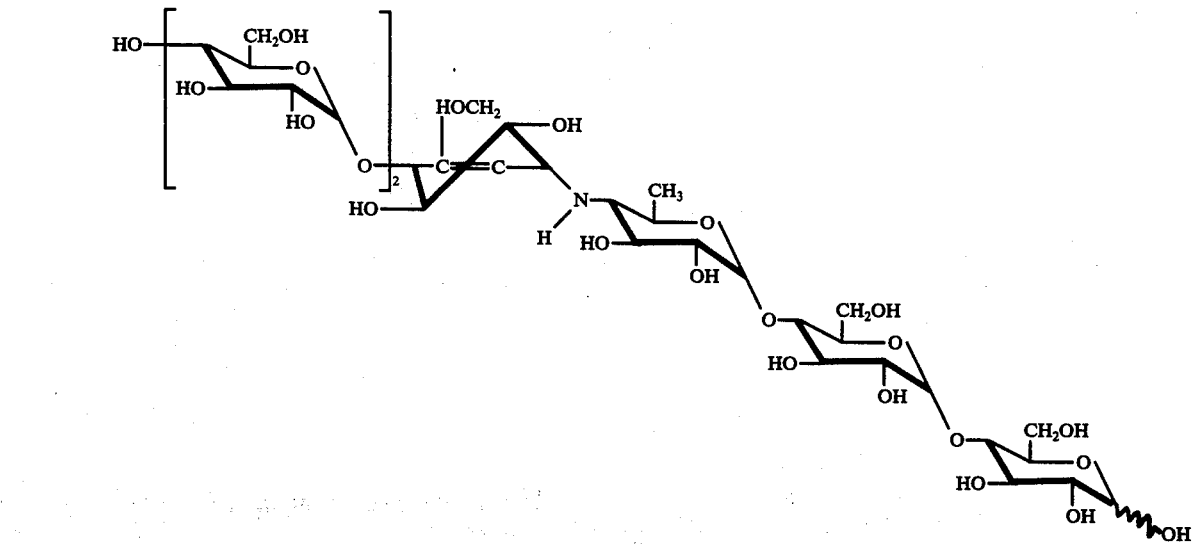

20. An amino sugar according to claim 17 wherein $n$ is 5.
21. An amino sugar according to claim 20 which has the formula:
22. An amino sugar according to claim 17 wherein $n$ is 6.
23. An amino sugar according to claim 22 which has the formula:
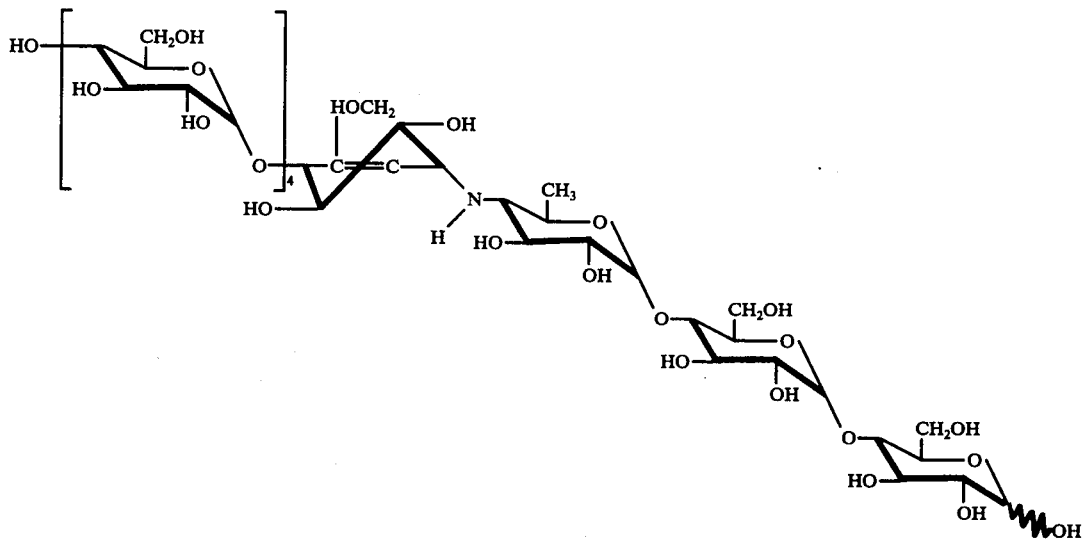
24. An amino sugar according to claim 17 wherein $n$ is 7.
25. An amino sugar according to claim 24 which has the formula:
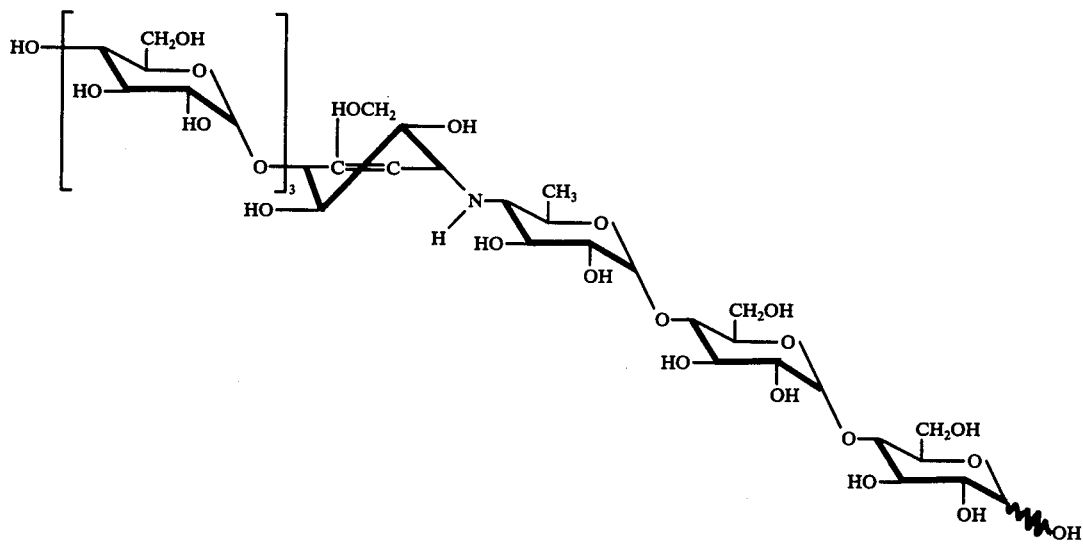

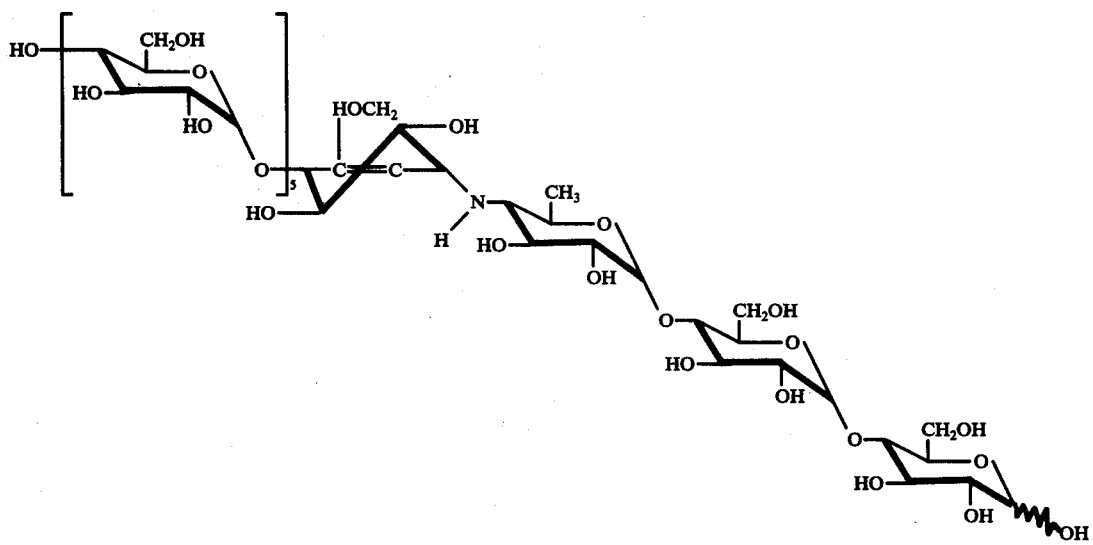

26. An amino sugar according to claim 17 wherein $n$ is 8.

27. An amino sugar according to claim 26 which has the formula:

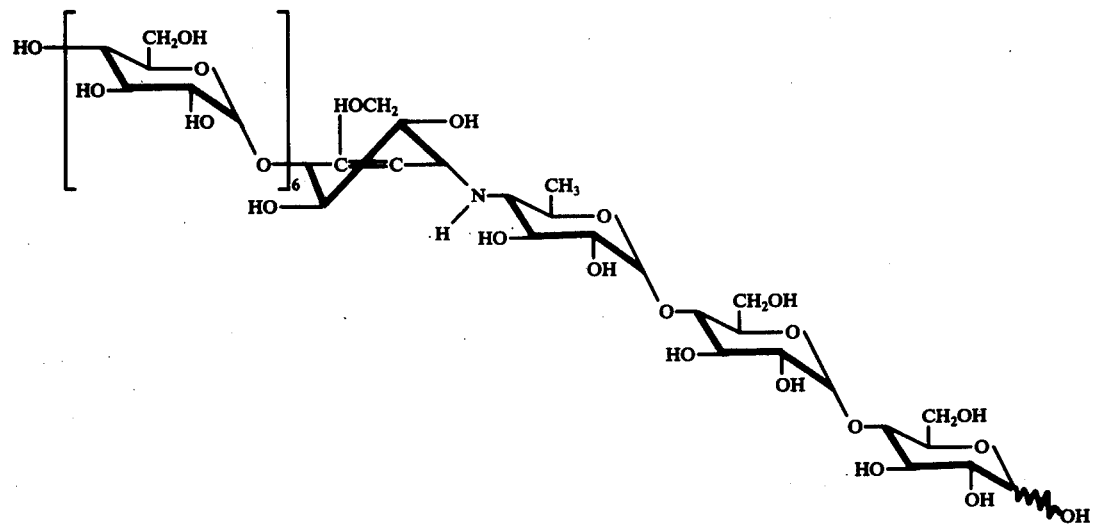

28. The method of inhibiting glucoside hydrolases in the digestive tract of humans and animals which comprises administering thereto at least an effective inhibitory amount of an amino sugar according to claim 17.

29. A pharmaceutical composition for effecting inhibition of glucoside hydrolases in humans and animals comprising an effective inhibitory amount of amino sugar according to claim 17 in combination with an inert, compatible pharmaceutical carrier.

30. A foodstuff composition for effecting inhibition of glucoside hydrolases in humans and animals comprising an effective inhibitory amount of amino sugar according to claim 17 in combination with an inert, compatible foodstuff carrier.

* * * * *

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 9, line 45, structural formula No. 4 should read as follows:

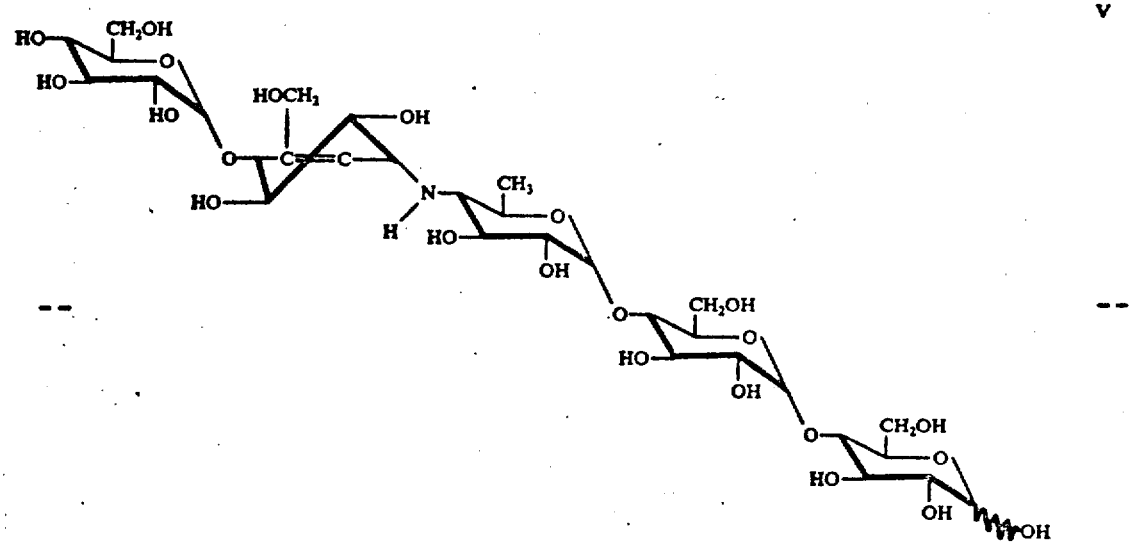

Column 17, line 1, "The produce" should read --To produce --.

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 34, lines 30-40, the structural formula should read as follows:

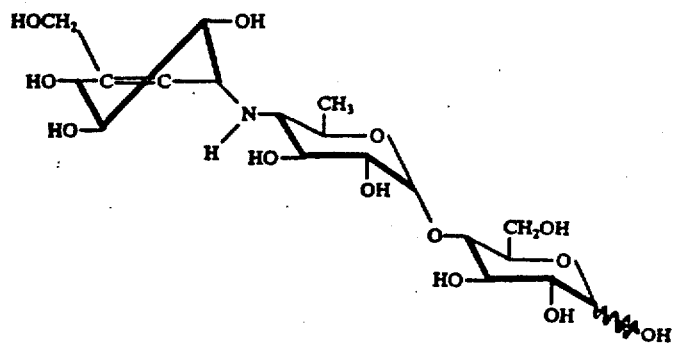

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 37, lines 1-21, structural formula of claim 13 should read as follows:

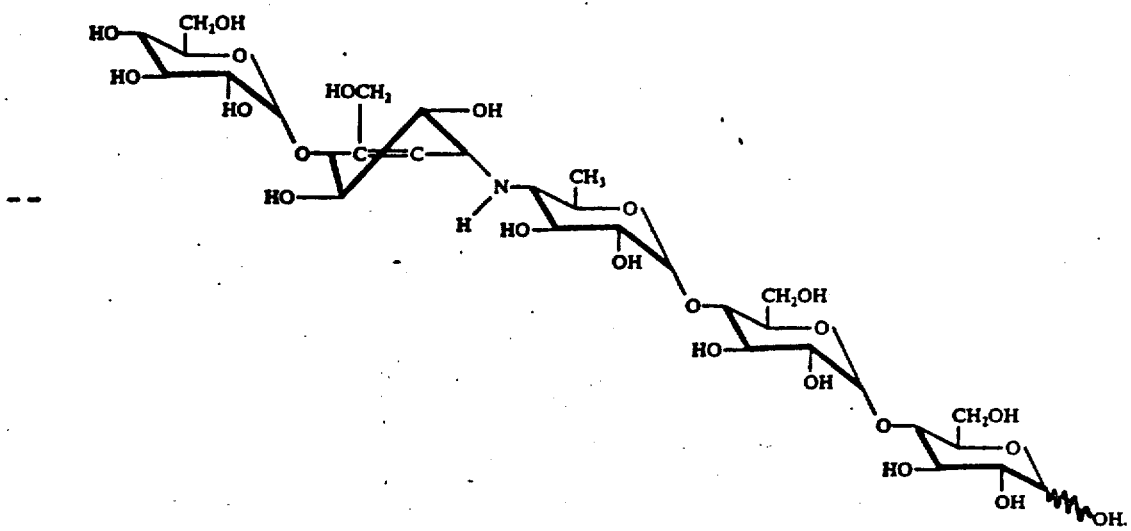

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

Page 4 of 9

It is certified that error appears in the above-identified patent and that said Letters Patent are hereby corrected as shown below:

Column 38, lines 27-35, the structural formula should read as follows:

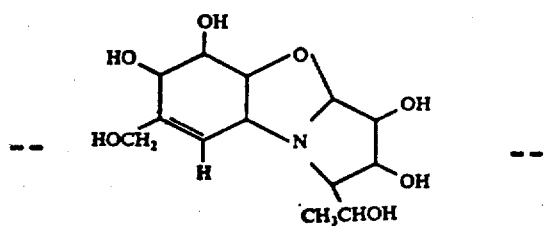

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above—identified patent and that said Letters Patent are hereby corrected as shown below:

Column 38, line 43, structural formula of claim 19 should read as follows:

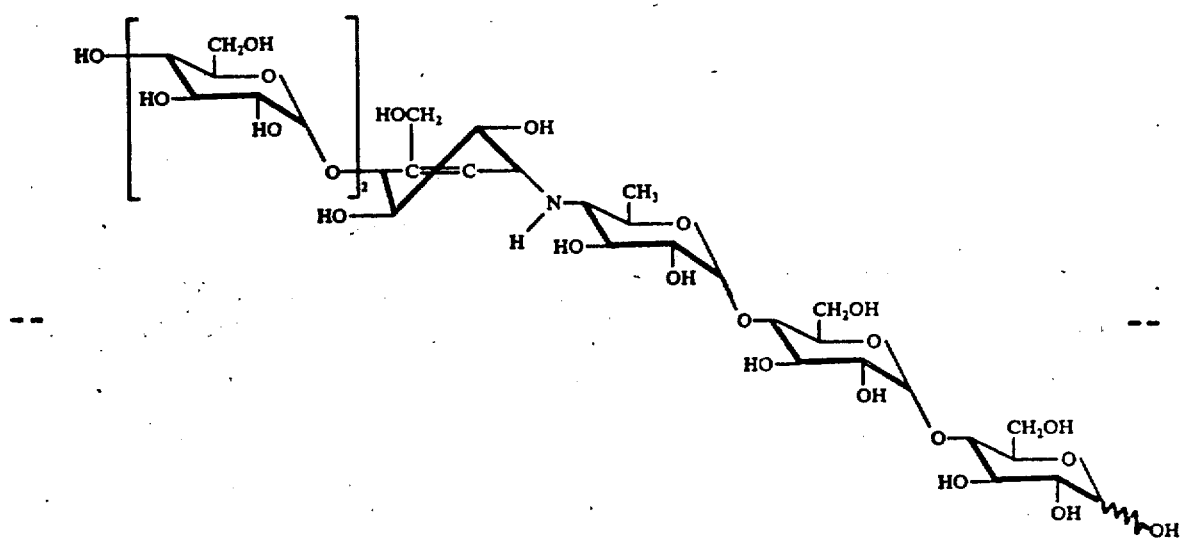

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 39, lines 36 to 65, structural formula for claim 21 should read as follows:

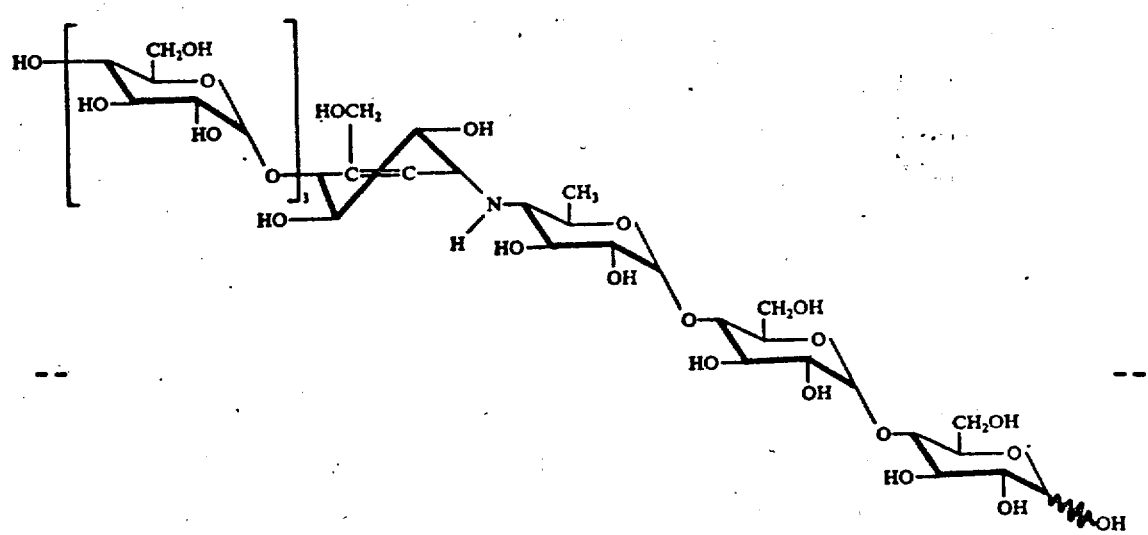

UNITED STATES PATENT AND TRADEMARK OFFICE
CERTIFICATE OF CORRECTION

PATENT NO. : 4,062,950

DATED : December 13, 1977

INVENTOR(S) : Werner Frommer et al.

It is certified that error appears in the above-identified patent and that said Letters Patent are hereby corrected as shown below:

Column 40, lines 3 to 30, structural formula of claim 23 should read as follows:

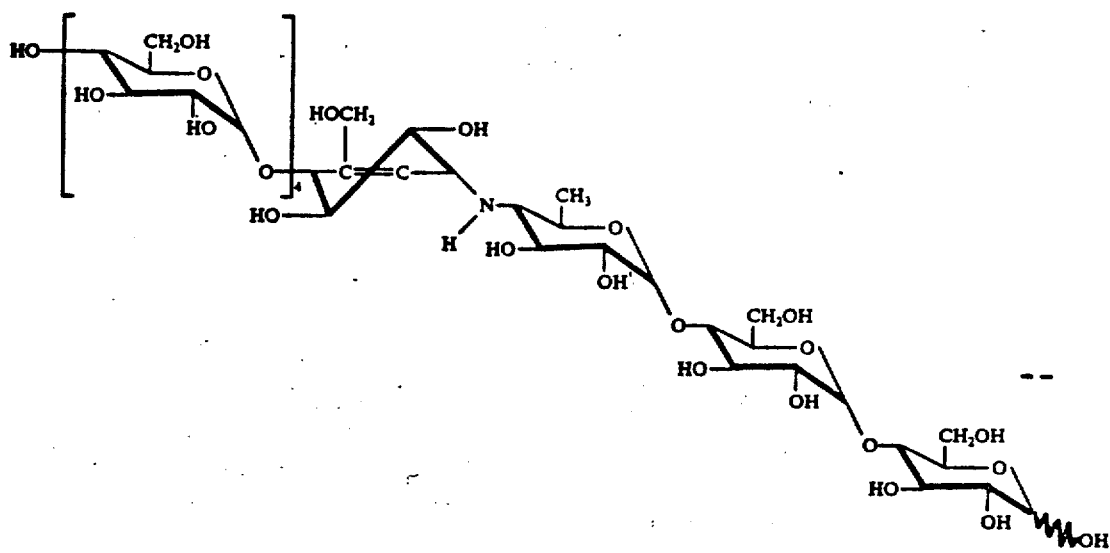

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 41, lines 1 to 22, structural formula for claim 25 should read as follows:

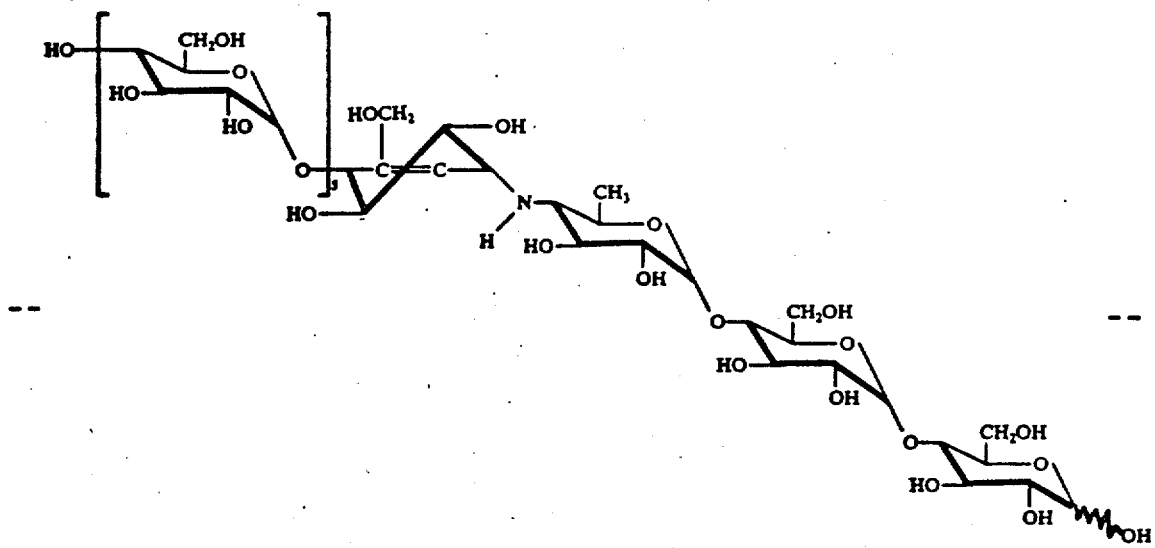

UNITED STATES PATENT AND TRADEMARK OFFICE
CERTIFICATE OF CORRECTION

PATENT NO. : 4,062,950
DATED : December 13, 1977
INVENTOR(S) : Werner Frommer et al.

It is certified that error appears in the above-identified patent and that said Letters Patent are hereby corrected as shown below:

Column 41, lines 27-49, structural formula for claim 27 should read as follows:

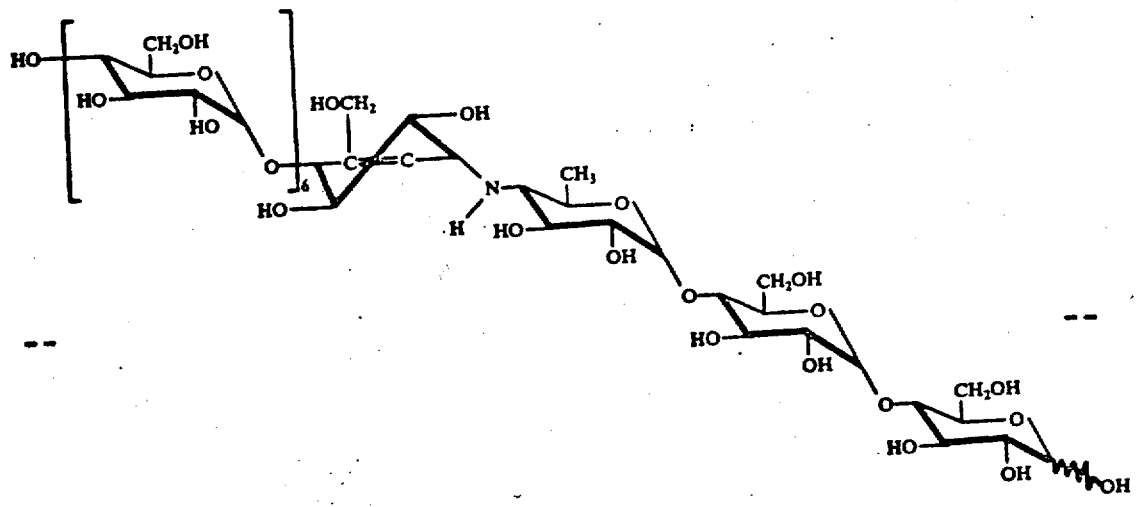

Signed and Sealed this

Eleventh Day of July 1978

[SEAL]

Attest:

RUTH C. MASON
Attesting Officer

DONALD W. BANNER
Commissioner of Patents and Trademarks